US012760076B2

(12) United States Patent
Shigemura et al.

(10) Patent No.: US 12,760,076 B2
(45) Date of Patent: *Oct. 13, 2026

(54) PHOTORESPONSIVE PROTEIN FOR COLOR RECOGNITION AND USE THEREOF

(71) Applicant: NAGOYA INSTITUTE OF TECHNOLOGY, Nagoya (JP)

(72) Inventors: Shunta Shigemura, Nagoya (JP); Shoko Hososhima, Nagoya (JP); Satoshi Tsunoda, Nagoya (JP); Hideki Kandori, Nagoya (JP)

(73) Assignee: NAGOYA INSTITUTE OF TECHNOLOGY, Nagoya (JP)

( * ) Notice: Subject to any disclaimer, the term of this patent is extended or adjusted under 35 U.S.C. 154(b) by 844 days.

This patent is subject to a terminal disclaimer.

(21) Appl. No.: 17/911,368

(22) PCT Filed: Mar. 15, 2021

(86) PCT No.: PCT/JP2021/010440

§ 371 (c)(1),
(2) Date: Sep. 13, 2022

(87) PCT Pub. No.: WO2021/182646

PCT Pub. Date: Sep. 16, 2021

(65) Prior Publication Data

US 2023/0104240 A1 Apr. 6, 2023

(30) Foreign Application Priority Data

Mar. 13, 2020 (JP) ................................ 2020-044713

(51) Int. Cl.

| | |
|---|---|
| ***C07K 14/47*** | (2006.01) |
| ***A61K 38/00*** | (2006.01) |
| ***A61K 48/00*** | (2006.01) |
| ***C12N 15/62*** | (2006.01) |
| ***C12N 15/85*** | (2006.01) |

(52) U.S. Cl.

CPC ........ *C07K 14/4722* (2013.01); *C12N 15/625* (2013.01); *C12N 15/85* (2013.01); *A61K 38/00* (2013.01); *A61K 48/00* (2013.01); *C12N 2800/107* (2013.01)

(58) Field of Classification Search

None

See application file for complete search history.

(56) References Cited

U.S. PATENT DOCUMENTS

| | | | | |
|---|---|---|---|---|
| 12,030,917 | B2 * | 7/2024 | Shigemura .............. | A61P 27/02 |
| 2013/0281379 | A1 | 10/2013 | Bamberg et al. | |
| 2022/0073571 | A1 | 3/2022 | Shigemura et al. | |
| 2023/0104240 | A1 | 4/2023 | Shigemura et al. | |

FOREIGN PATENT DOCUMENTS

| | | | |
|---|---|---|---|
| EP | 3 851 534 | A1 | 7/2021 |
| IN | 201917011849 | A | 7/2019 |
| JP | 2009-536219 | A | 10/2009 |
| JP | 2013-544494 | A | 12/2013 |
| WO | 2007/131180 | A2 | 11/2007 |
| WO | 2012/032103 | A1 | 3/2012 |
| WO | 2020/054868 | A1 | 3/2020 |

OTHER PUBLICATIONS

Lectures and oral presentations—Hidaki Kamitori, available online at https://researcher.nitech.ac.jp/html/96_knkyu_prsn_20_en.html, 2 pages (accessed on Nov. 27, 2025) (Year: 2025).*
Shigemura et al., Appl. Sci. 9:13 pages (Aug. 2019) (Year: 2019).*
GenBank Accession No. ARQ20888, 1 page (2017) (Year: 2017).*
Oct. 2, 2025 Office Action issued in European Patent Application No. 21 766 945.6.
Mar. 4, 2024 Search Report issued in European Patent Application No. 21766945.6.
Anonymous; "Uniprot: A0A172M4H4"; Sep. 7, 2016; XP093133349.
Anonymous; "Uniprot: A0A0G4F4D6"; Sep. 16, 2015; XP093133457.
Anonymous; "Uniprot: A0A3G1I4H9: Cation channel rhodopsin4"; Feb. 13, 2019; XP093133331.
Oct. 20, 2023 Office Action Issued in Chinese Patent Application No. 202180028549.X.
Mar. 18, 2025 Office Action issued in Japanese Patent Application No. 2022-506869.
Yamauchi et al.; "Molecular properties of DTD channelrhodopsin from Guillardia theta;" Biophysics and Physicobiology; 2017; pp. 57-66; vol. 14.
Hososhima et al.; "Novel optogenetics tool: Gt_CCR4, a light-gated cation channel with high reactivity to weak light;" Biophysical Reviews; 2020; pp. 453-459; vol. 12.
Carter et al.; "Manipulating Neural Activity;" Guide to Research Techniques in Neuroscience (Second Edition); Chapter 8; 2015; pp. 185-201.
Apr. 27, 2021 Search Report issued in International Patent Application No. PCT/JP2021/010440.
Apr. 27, 2021 Written Opinion of the International Searching Authority issued in International Patent Application No. PCT/JP2021/010440.
Jan. 15, 2025 Office Action issued in European Patent Application No. 21766945.6.
Dai et al., "Long-term retinal cone rescue using a capsid mutant AAV8 vector in a mouse model of CNGA3-achromatopsia", 2017, PLOS One, vol. 12, No. 11.
Curtis et al.; "Algal genomes reveal evolutionary mosaicism and the fate of nucleomorphs;" Nature; 2012; pp. 59-65; vol. 492.

(Continued)

*Primary Examiner* — Thea D' Ambrosio
(74) *Attorney, Agent, or Firm* — Oliff PLC

(57) ABSTRACT

A protein for visual color recognition and the like, the protein having a channel activity and including an amino acid residue different from the amino acid residue present in a first amino acid sequence represented by SEQ ID NO: 1, at a position or positions corresponding to one or two or more selections from the group consisting of the following positions in the first amino acid sequence: positions 53, 83, 87, 117, 120, 124, 137, 139, 142, 143, 146, 150, 169, 173, 177, 198, 204, 216, 217, 218, 231, 238, 245, and 247.

7 Claims, 10 Drawing Sheets

Specification includes a Sequence Listing.

(56) References Cited

OTHER PUBLICATIONS

Yamauchi et al.; "Gene expression analysis of 44 microbial rhodopsin-like proteins from marine algae Gullardia theta;" Seibutsu Butsuri; 2018; p. S376; vol. 58, No. Supplements 1-2.
Bi et al.; Ectopic expression of a microbial-type rhodopsin restores visual responses in mice with photoreceptor degeneration; Neuron; 2006; pp. 23-33; vol. 50.
Nagel et al.; "Channelrhodopsin-1: a light-gated proton channel in green algae;" Science; 2002; pp. 2395-2398; vol. 296, No. 5577.
Nagel et al., "Channelrhodopsin-2, a directly light-gated cation-selective membrane channel;" Proc Natl Acad Sci U S A;. 2003; pp. 13940-13945; vol. 100, No. 24.
Boyden et al., "Millisecond-timescale, genetically targeted optical control of neural activity;" Nat Neurosci.; 2005; pp. 1263-1268; vol. 8, No. 9.
Lagali et al.; "Light-activated channels targeted to ON bipolar cells restore visual function in retinal degeneration;" Nat Neurosci.; 2008; pp. 667-675; vol. 11, No. 6.
Tomita et al.; "Visual properties of transgenic rats harboring the channelrhodopsin-2 gene regulated by the thy-1.2 promoter;" PLoS One; 2009; vol. 4, No. 11.
Busskamp et al.; "Genetic reactivation of cone photoreceptors restores visual responses in retinitis pigmentosa;" Science; 2010; pp. 413-417; vol. 329, No. 5990.
Watanabe et al.; "Structural model of channelrhodopsin;" J Biol Chem; 2012; pp. 7456-7466; vol. 287, No. 10.
Kato et al.; "Crystal structure of the channelrhodopsin light-gated cation channel;" Nature; 2012; pp. 369-374; vol. 482, No. 7385.
Wietek et al., "Conversion of channelrhodopsin into a light-gated chloride channel;" Science; 2014; pp. 409-412; vol. 344, No. 6182.
Tomita et al.; "Restoration of the majority of the visual spectrum by using modified Volvox channelrhodopsin-1;" Mol Ther.; 2014; pp. 1434-1440; vol. 22, No. 8.
Sengupta et al.; "Red-shifted channelrhodopsin stimulation restores light responses in blind mice, macaque retina, and human retina;" EMBO Mol Med.; 2016; pp. 1248-1264; vol. 8, No. 11.
Sato et al., "Visual Responses of Photoreceptor-Degenerated Rats Expressing Two Different Types of Channelrhodopsin Genes;" Sci Rep.; 2017; pp. 1-10; vol. 7, No. 41210.
Govorunova et al.; "Structurally Distinct Cation Channelrhodopsins from Cryptophyte Algae;" Biophys J.; 2016; pp. 2302-2304; vol. 110, No. 11.
Volkov et al.; "Structural insights into ion conduction by channelrhodopsin 2;" Science; 2017; pp. 1018-1027; vol. 358, No. 6366.
Kim et al., "Crystal structure of the natural anion-conducting channelrhodopsin GtACR1;" Nature; 2018; pp. 343-348; vol. 561, No. 7723.
Nov. 5, 2019 Search Report issued in International Patent Application No. PCT/JP2019/036230.
Nov. 5, 2019 Written Opinion of the International Searching Authority issued in International Patent Application No. PCT/JP2019/036230.
Feb. 15, 2022 Office Action issued in Japanese Patent Application No. 2020-546237.
Klapoetke, N. et al., "Independent optical excitation of distinct neural populations," Nature Methods, vol. 11, No. 3, pp. 338-346, Mar. 2014.
Jun. 20, 2022 extended Search Report issued in European Patent Application No. 19861044.6.
Sep. 28, 2022 Office Action Issued in Chinese Patent Application No. 201980060124.X.
Oct. 18, 2022 Office Action Issued in Japanese Patent Application No. 2020-546237.
Otomo et al. The primary structures of helices A to G of three bacteriorhodopsin-like retinal proteins. Journal of General Microbiology. 1992, vol. 138, pp. 2389-2396. (Year: 1992).
U.S. Appl. No. 18/669,628, filed May 21, 2024 in the name of Shigemura et al.

* cited by examiner

Spectra of visual pigments in human rod and cone cells (A) Maximum activity wavelengths λmax_act of Gt_CCR4 mutants

| Mutant | λmax_act (nm) | Mutant | λmax_act (nm) |
|---|---|---|---|
| L53N | 540 | S247A | 515 |
| V83A | 540 | S247M | 530 |
| Y117A | 480/510 | L146A/C150A | 530 |
| Y117F | 500 | L146A/G169S | 535 |
| Y117N | 510 | L146A/W177Y | 530 |
| K137A | 530 | L146A/Y217F | 490 |
| L146A | 530 | L146A/P218A | 520 |
| C150A | 520 | L146A/P218G | 525 |
| G169S | 510 | L146A/P218S | 530 |
| W177Y | 510 | L146A/P218T | 510/560 |
| K198A | 535 | L146A/T238V | 520 |
| Y217F | 475 | T147C/G151A | 510 |
| P218A | 530 | V83A/L146A/P218T | 540 |
| P218T | 510 | T147C/G151A/Y217F | 470 |
| A245M | 525 | | |

| Mutant | 440nm/λmax | 600nm/ λ max |
|---|---|---|
| WT | 0.31 | 0.17 |
| L53N | 0.40 | 0.23 |
| V83A | 0.46 | 0.34 |
| Y117A | 0.56 | 0.09 |
| Y117F | 0.56 | 0.09 |
| Y117N | 0.47 | 0.16 |
| K137A | 0.32 | 0.21 |
| L146A | 0.53 | 0.45 |
| C150A | 0.56 | 0.21 |
| G169S | 0.52 | 0.32 |
| W177Y | 0.45 | 0.26 |
| K198A | 0.31 | 0.18 |
| Y217F | 0.71 | 0.15 |
| P218A | 0.25 | 0.27 |
| P218T | 0.34 | 0.44 |
| A245M | 0.25 | 0.16 |
| S247A | 0.57 | 0.24 |
| S247M | 0.27 | 0.19 |
| L146A/C150A | 0.53 | 0.47 |
| L146A/G169S | 0.55 | 0.55 |
| L146A/W177Y | 0.49 | 0.43 |
| L146A/Y217F | 0.71 | 0.25 |
| L146A/P218A | 0.46 | 0.48 |
| L146A/P218G | 0.51 | 0.61 |
| L146A/P218S | 0.40 | 0.36 |
| L146A/P218T | 0.59 | 0.74 |
| L146A/T238V | 0.47 | 0.29 |
| T147C/G151A | 0.56 | 0.03 |
| V83A/L146A/P218T | 0.34 | 0.50 |
| T147C/G151A/Y217F | 0.50 | 0.00 |

Gt_CCR4 Channel activity

Gt_CCR4 Single mutant channel activity

Light irradiation:ChR2: Wavelength 488nm(Light intensity 6.88mW/mm$^2$)
Gt_ CCR4: Wavelength 530nm(Light intensity 6.88mW/mm$^2$)

Photostimulation of neural activity in primary cultured rat cerebral epithelial cells and Dependence on the light intensity

SEQUENCE LISTING

<160> NUMBER OF SEQ ID NOS: 6

<210> SEQ ID NO 1
<211> LENGTH: 367
<212> TYPE: PRT
<213> ORGANISM: Guillardia thetaS

<400> SEQUENCE: 1

Met Thr Thr Ser Ala Pro Ser Leu Ser Asp Pro Asn Trp Gln Tyr Gly
1 5 10 15

Met Gly Gly Trp Asn Asn Pro Arg Leu Pro Asn Phe Asn Leu His Asp
20 25 30

Pro Thr Val Ile Gly Val Asp Trp Leu Gly Phe Leu Cys Leu Leu Gly
35 40 45

Ala Ser Leu Ala Leu Met Tyr Lys Leu Met Ser Phe Lys Gly Pro Asp
50 55 60

Gly Asp Gln Glu Phe Phe Val Gly Tyr Arg Glu Glu Lys Cys Leu Ser
65 70 75 80

Ile Tyr Val Asn Leu Ile Ala Ala Ile Thr Tyr Trp Gly Arg Ile Cys
85 90 95

Ala His Phe Asn Asn Asp Met Gly Leu Ser Leu Ser Val Asn Tyr Phe
100 105 110

Lys Tyr Leu Asp Tyr Ile Phe Thr Cys Pro Ile Leu Thr Leu Asp Leu
115 120 125

Leu Trp Ser Leu Asn Leu Pro Tyr Lys Ile Thr Tyr Ser Leu Phe Val
130 135 140

Gly Leu Thr Ile Ala Cys Gly Val Phe Cys Asn Ala Phe Glu Pro Pro
145 150 155 160

Ala Arg Tyr Leu Trp Phe Met Phe Gly Cys Phe Ile Phe Ala Phe Thr
165 170 175

Trp Ile Ser Ile Ile Arg Leu Val Tyr Ala Arg Phe Gln Gln Phe Leu
180 185 190

Asn Glu Asp Ala Lys Lys Ile Arg Ala Pro Leu Lys Leu Ser Leu Thr
195 200 205

Leu Tyr Phe Ser Ile Trp Cys Gly Tyr Pro Ala Leu Trp Leu Leu Thr
210 215 220

Glu Phe Gly Ala Ile Ser Gln Leu Ala Ala His Val Met Thr Val Ile
225 230 235 240

Met Asp Val Ala Ala Lys Ser Val Tyr Gly Phe Ala Leu Leu Lys Phe
245 250 255

Gln Leu Gly Val Asp Lys Arg Asp Val Trp Leu Asp Glu Leu Lys Ser
260 265 270

Val Arg Tyr Arg Asp Val Val Pro Gln Ile Arg Pro Ser Lys Thr Arg
275 280 285

Glu Ser Arg Met Glu Tyr Ser Glu Asp Gly Asp Phe Met Arg Pro Ser
290 295 300

Lys Gly Lys Arg Ala Glu Gly Asp Tyr Met Asn Pro Arg Trp Asp His
305 310 315 320

His Asp Asp Gly Arg Arg Leu Pro Asp Ser Arg Glu Met Asp Glu Gln
325 330 335

Val His Glu Lys Asp Gln Glu Ile Ser Ser Thr Met Lys Gln Ile Ala
340 345 350

Asp Leu Asn Lys Gln Leu Ser Ala Met Gln Glu Ser Glu Ala Val
355 360 365

<210> SEQ ID NO 2
<211> LENGTH: 1101
<212> TYPE: DNA
<213> ORGANISM: Guillardia theta

<400> SEQUENCE: 2

```
atgacgacgt ctgccccttc actctccgat cccaactggc aatatggcat gggaggatgg     60

aacaatcctc gccttccaaa cttcaatctt cacgacccga ccgtgatcgg agttgattgg    120

ctgggatttc tttgtcttct tggtgcctct ctcgccctca tgtacaagct catgtcgttc    180

aagggccccg atggcgacca agagttcttc gtcggctacc gggaagagaa gtgcctctcc    240

atctacgtca acctcatcgc tgccatcacc tactggggcc gtatctgcgc tcacttcaac    300

aatgacatgg gcctttctct gtctgtcaac tacttcaagt acctggacta catcttcacc    360

tgtcctatcc tgacgctgga tctgctgtgg tcgctcaacc tcccctacaa gatcacctac    420

tctctcttcg tcggattgac catcgcatgc ggagtcttct gcaacgcgtt cgagcctccc    480

gcgcggtacc tctggttcat gttcggctgc ttcatctttg ccttcacgtg gatcagcatc    540

atccgcctcg tctacgcgcg gttccagcag tttctcaacg aggacgcgaa gaagatccga    600

gcgcctctca agctctccct caccctctac ttcagcatct ggtgcggcta cccggccctc    660

tggcttctca ccgagttcgg agccatctcc cagctggcag cccacgtgat gactgtcatc    720

atggacgtcg ccgccaagtc tgtgtacggc ttcgccctgc tcaagttcca gctgggggtg    780

gacaagcgag acgtctggct cgatgagctc aagagcgtca ggtatcgtga cgtcgtccct    840

cagatccgac cgtcgaagac gcgagagagc cgcatggagt attcagagga cggagatttc    900

atgcgtccga gcaaggggaa gagggcggaa ggagactaca tgaaccctcg ctgggaccac    960

catgacgatg ggaggaggct gcccgacagc cgggagatgg acgagcaagt gcacgagaag   1020

gaccaggaga tctcgtcgac gatgaagcag atcgccgacc tcaacaagca gctctctgcc   1080

atgcaggagt ccgaggccgt t                                             1101
```

<210> SEQ ID NO 3
<211> LENGTH: 36
<212> TYPE: DNA
<213> ORGANISM: Artificial sequence
<220> FEATURE:
<223> OTHER INFORMATION: Priemer

<400> SEQUENCE: 3

```
cgagctcaag cttatgatga caacaagcgc ccctag                               36
```

<210> SEQ ID NO 4
<211> LENGTH: 35
<212> TYPE: DNA
<213> ORGANISM: Artificial sequence
<220> FEATURE:
<223> OTHER INFORMATION: Priemer

<400> SEQUENCE: 4

```
gaccggtgga tcctgaacag cctcagactc ttgca                                35
```

<210> SEQ ID NO 5
<211> LENGTH: 21
<212> TYPE: DNA
<213> ORGANISM: Artificial sequence
<220> FEATURE:
<223> OTHER INFORMATION: Priemer

<400> SEQUENCE: 5

-continued

```
cataagcttg agctcgagat c                                               21


<210> SEQ ID NO 6
<211> LENGTH: 21
<212> TYPE: DNA
<213> ORGANISM: Artificial sequence
<220> FEATURE:
<223> OTHER INFORMATION: Priemer

<400> SEQUENCE: 6

caggatccac cggtcgccac c                                               21
```

PHOTORESPONSIVE PROTEIN FOR COLOR RECOGNITION AND USE THEREOF

CROSS-REFERENCE TO RELATED APPLICATION

This application is a related application to Japanese Patent Application No. 2020-44713 filed Mar. 13, 2020, and claims priority based on same, the contents of which are incorporated herein by reference in their entirety.

TECHNICAL FIELD

This Description relates to a photoreceptor protein for color recognition or a mutant thereof, and to the use thereof.

BACKGROUND ART

Retinitis pigmentosa and age-related macular degeneration are examples of eye diseases that cause blindness. In these diseases, the eventual outcome of blindness is the result of the degeneration and death of rod cells and cone cells, which are photoreceptor cells in the retina. Of these diseases, retinitis pigmentosa is a genetic disease, and more than 100 causative genes have been reported. This means that the mechanism of action leading to rod cell and cone cell degeneration and death varies widely from patient to patient, and that the establishment of a clear clinical treatment regimen is thus problematic. The present situation is that practical treatment regimens have not been established. Genetic factors are also considered to be present with age-related macular degeneration, and a plurality of related genes have been reported.

Light signals from the ambient environment are received and converted into electrical signals by the rod cells and cone cells in the retina. These signals reach the retina neurons such as bipolar cells and retina ganglion cells, optic nerve, and visual cortex of the cerebral cortex and are recognized as images.

Rhodopsins and opsins or color visual pigments in the rod cells and cone cells are responsible for converting the light signals to electrical signals. At the present time, research is being carried out with respect to retinitis pigmentosa, etc., with the goal of treatments that recover visual function in patients by the introduction, for example, of a gene encoding the channelrhodopsin 2 (ChR2) originating from the phototactic algae Chlamydomonas into the remaining retinal ganglion cells, thereby imparting a photoreceptive capability to these cells (PTL 1, PTL 2).

CITATION LIST

Patent Literature

[PTL 1] WO 2007/131180
[PTL 2] WO 2012/032103

SUMMARY

Technical Problem

ChR2 is a light-gated cation channel (photoreceptor protein) that, when illuminated, takes in (transports) $Na^{+}$ and $Ca^{2+}$ from outside the cell to inside the cell, or from inside the cell to outside the cell. ChR2 is thus a protein that can produce, with the protein molecule alone, a change in membrane potential when light is applied.

However, the restoration of patient visual function is still unsatisfactory even with algae-derived ChR2. For example, it is also important for the restoration of visual function to achieve a more appropriate recognition—accompanying color-related information—of external information that is originally chromatic color.

This Description provides a photoreceptor protein for visual color recognition, and a use thereof.

Solution to Technical Problem

The present inventors discovered that advantageous characteristics with regard to color recognition are possessed by mutants of a channelrhodopsin that is a certain type of cation channel derived from the crvptophyte *Guillardia theta* (*G. theta*). This Description provides the following means based on this knowledge.

[1] A protein having a channel activity and comprising an amino acid residue different from the amino acid residue present in a first amino acid sequence represented by SEQ ID NO: 1, at a position or positions corresponding to one or two or more selections from the group consisting of the following positions in the first amino acid sequence: positions 53, 83, 87, 117, 120, 124, 137, 139, 142, 143, 146, 147, 150, 151, 169, 173, 177, 198, 204, 216, 217, 218, 231, 238, 245, and 247.

[2] The protein according to [1], wherein said position or positions is or are one or two or more selections from the group consisting of positions 87, 117, 120, 124, 139, 142, 143, 146, 150, 169, 173, 177, 217, 218, 238, 245, and 247.

[3] The protein according to [1], wherein said position or positions is or are one or two or more selections from the group consisting of positions 53, 83, 137, 146, 147, 151, 169, 177, 217, 218, and 247.

[4] The protein according to [3], wherein said position or positions is or are one or two or more selections from the group consisting of positions 169, 177, 217, 218, and 247.

[5] The protein according to [4], wherein said position is position 217.

[6] The protein according to [3], wherein said position or positions is or are position 147 and/or position 151.

[7] The protein according to [6], wherein said position or positions is or are positions 147 and 151.

[8] The protein according to any of [4] to [7], having a maximum activity wavelength of less than 520 nm.

[9] The protein according to [1], wherein said position or positions is or are one or two or more selections from the group consisting of positions 53, 83, 137, 146, and 218.

[10] The protein according to [9], wherein said position is position 146.

[11] The protein according to [10], wherein said position or positions is or are an additional one or two or more selections from the group consisting of positions 150, 169, 177, and 218.

[12] The protein according to any of [9] to [11], having a maximum activity wavelength of at least 530 nm.

[13] The protein according to [1] or [2], wherein said position or positions is or are one or two or more selections from the group consisting of positions 137, 146, 150, 177, 198, 238, 245, and 247.

[14] The protein according to [13], having a maximum activity wavelength of greater than or equal to 520 nm and less than 530 nm.

[15] The protein according to wherein said position or positions is or are one or two or more selections from the group consisting of positions 150, 169, 177, 218, and 247.

[16] The protein according to [1] wherein said position or positions is or are one or two or more selections from the group consisting of positions 87, 117, 120, 124, 139, 142, 143, 173, 204, 216, and 231.

[17] The protein according to any of [1] to [16], further comprising a deletion, substitution, or insertion of one or several amino acid residues.

[18] The protein according to any of [1] to [17], wherein the protein comprises an amino acid substitution according to any of the following modes, at a position corresponding to a position as follows in the first amino acid sequence.

TABLE 1

| position in first amino acid sequence | amino acid substitution mode | | | |
|---|---|---|---|---|
| 53 | L53N | | | |
| 83 | V83A | | | |
| 137 | K137A | | | |
| 146 | L146A | | | |
| 150 | C150A | | | |
| 169 | G169S | | | |
| 177 | W177Y | | | |
| 198 | K198A | | | |
| 217 | Y217F | Y217N | | |
| 218 | P218A | P218S | P218G | P218T |
| 238 | T238V | | | |
| 245 | A245M | | | |
| 247 | S247A | S247M | | |
| 146/150 | L146A/C150A | | | |
| 146/169 | L146A/G169S | | | |
| 146/177 | L146A/W177Y | | | |
| 146/217 | L146A/Y217F | | | |
| 147/218 | L146A/P218A | L146A/P218T | L146A/P218S | L146A/P218G |
| 146/238 | L146A/T238V | | | |
| 83/146/218 | V83A/L146A/P218A | | | |
| 147 | T147C | | | |
| 147/151 | T147C/G151A | | | |
| 147/151/217 | T147C/G151A/Y217F | | | |

[19] The protein according to any of [1] to [18], wherein the protein comprises an amino acid substitution according to any of the following modes, at a position corresponding to a position as follows in the first amino acid sequence.

TABLE 2

| position in first amino acid sequence | amino acid substitution mode | | | |
|---|---|---|---|---|
| 53 | L53A | | | |
| 83 | V83T | | | |
| 87 | A87S | | | |
| 117 | Y117A | Y117D | Y117F | Y117N |
| 124 | L124Q | L124C | L124T | L124A |
| 142 | L142A | | | |
| 204 | K204A | | | |
| 216 | G216S | | | |
| 231 | Q231L | | | |
| 137/204 | K137A/K204A | | | |
| 146/218 | L146A/P218C | L146A/P218H | L146A/P218N | L146A/P218V |

[20]. The protein according to any of [1] to [19], for which a first ratio, this being a value corresponding to a channel activity at 440 nm relative to the value corresponding to the channel activity at the wavelength (λmax) at which the protein exhibits its maximum channel activity, is greater than or equal to 0.4.

[21] The protein according to any of [1] to [20], for which a second ratio, this being a value corresponding to a channel activity at 600 nm relative to the value corresponding to the channel activity at the wavelength (λmax) at which the protein exhibits its maximum channel activity, is greater than or equal to 0.4.

[22] The protein according to any of [1] to [21], wherein the amino acid sequence of the protein has 90% or more identity with the first amino acid sequence.

[23] A method of use to improve or recover a photosensitivity for color recognition of a retina, using a protein according to any of [1] to [22] or a polynucleotide that encodes said protein.

[24] A drug composition for the treatment or prevention of a visual impairment, comprising a protein according to any of [1] to [22] or a polynucleotide that encodes said protein.

[25] The drug composition according to [24], wherein the visual impairment is selected from the group consisting of retinitis pigmentosa, age-related macular degeneration, diabetic retinopathy, retinal detachment, and color vision abnormalities.

[26] A method for screening mutant proteins, comprising a step of evaluating a relationship between the wavelength of irradiated light and a channel activity for a test protein that is provided with an amino acid residue different from that in the first amino acid sequence represented by SEQ ID NO: 1, at one or two more positions in the first amino acid sequence.

[27] A method of use, comprising using a protein according to any of [1] to [22], or a polynucleotide that encodes said protein, to cause the firing of a muscle cell, cerebral epithelial neuron, or hippocampal neuron upon irradiation with light.

DESCRIPTION OF EMBODIMENTS

The disclosure according to this Description relates to a photosensitive photoreceptor protein for color recognition. It is based on the following findings: GtCCR4 (also referred to in the following as the first protein)—a cation photosensitive protein originating in *G. theta* that is composed of the amino acid sequence given by SEQ ID NO: 1 and that was discovered by the present inventors—exhibits a photosensitivity superior to that of the heretofore known ChR2 of Chlamydomonas origin, and mutations provided by the introduction of mutation into the first protein have activity spectra different from that of the first protein and have maximum activity wavelengths on the shorter wavelength side or longer wavelength side from the approximately 520 nm that is the maximum activity wavelength where the first protein exhibits its maximum channel activity.

Figure 1:
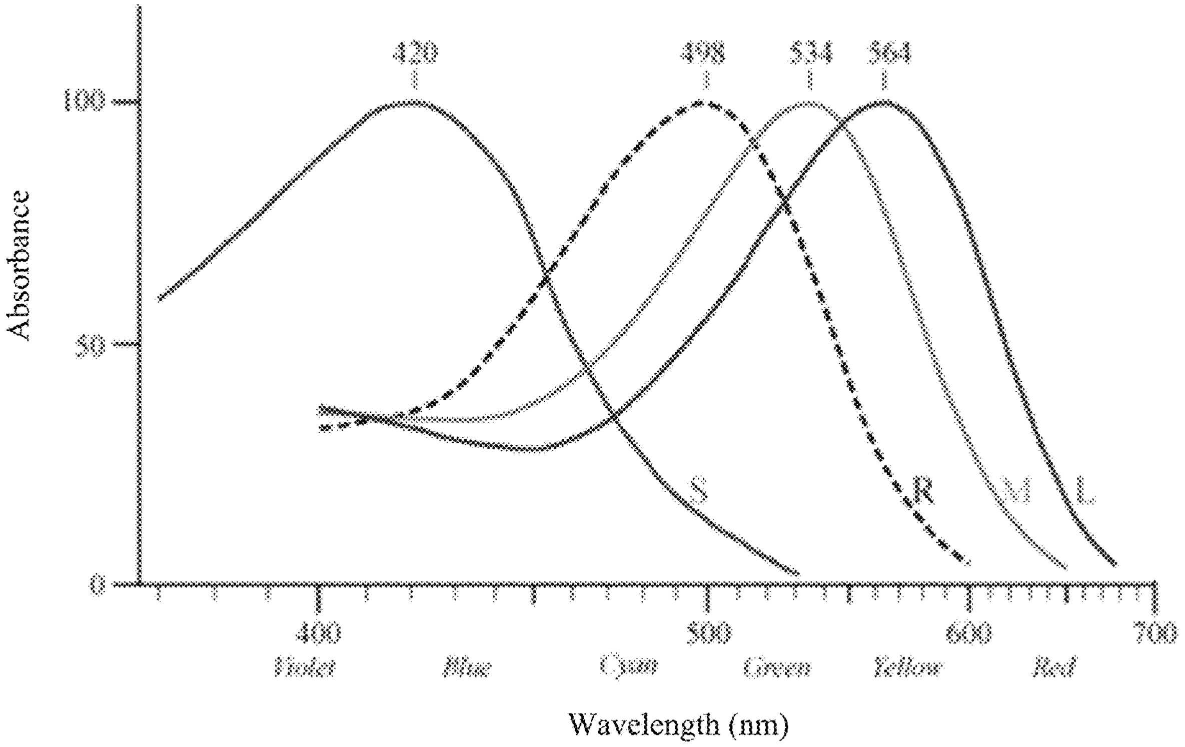
FIG. 1 is a diagram that shows the maximum activity wavelengths (λmax_act) of the visual pigments in human rod and cone cells, wherein the maximum activity wavelength (498 nm) of the visual pigment (R) in rod cells and the maximum activity wavelengths (420 nm, 534 nm, and 564 nm, respectively) of the three visual pigments (S, M, L) in cone cells are shown.

For example, as shown in the upper part of FIG. 1, rod visual pigment having a maximum activity wavelength of 498 nm, and cone pigments having maximum activity wavelengths of 420 nm, 534 nm, and 564 nm, are provided in the cell membranes of human rod cells and cone cells, respectively. Color recognition of external information is made possible by these three types of cone visual pigments.

Depending on its mode of mutation, the first protein mutant disclosed in the present Description (also referred to herebelow as the present mutant) can have a maximum channel activity at one or two or more wavelengths different from that of the first protein. That is, the present mutant, due to its mutation, can have a maximum activity wavelength or an activity spectrum that is different from that of the first protein. Through the expression of the present mutant in cell membranes in the retina, e.g., in ganglion cells and/or bipolar cells, these cells are equipped with an ion permeability (transportability) characteristic of the present mutant and in accordance with the wavelength of the light impinging on the cell membrane, and a channel activity is expressed based on this.

For example, use can be made of only one or two or more types of cells that respectively express a present mutant in the cell membrane, or use can be made of a combination of such present mutant-expressing cells with one or two or more types of other mutant-expressing cells that respectively express in the cell membrane a protein having a maximum activity wavelength or an activity spectrum different from that of the present mutant of, e.g., the first protein. The one or two or more types of cells that express the present mutant or other mutant can be exemplified by cells selected from cells such as ganglion cells, bipolar cells, amacrine cells, and horizontal cells. When the retina is provided with such present mutant-expressing cells, or other mutant-expressing cells in addition to the present mutant-expressing cells, these cells can then exhibit, in the retina, a channel activity in accordance with the incident light. As a result, the retina can ultimately acquire a light-response capability that can contribute to providing, or improving, color recognition in the brain.

The present protein, which is the origin of the present mutant, exhibits, inter glia, an excellent channel opening ratio, an excellent ion permeability (transportability) by channels constituted of the present protein, and an excellent expression level by the present protein on cell membranes in the retina, e.g., ganglion cells, bipolar cells, and so forth. Due to this, the present mutant can also exhibit a highly sensitive light-response capability for color recognition.

Through the introduction, using, e.g., a viral vector, of a polynucleotide, e.g., DNA, encoding the present mutant into retinal cells, for example, ganglion cells or bipolar cells, the present mutant can be expressed in cell membranes in the retina, for example, in ganglion cells or bipolar cells, and a high-sensitivity light-response capability for color recognition can be exhibited.

The present mutant, or a nucleotide encoding the present mutant, is thus useful for restoring vision in patients with eye diseases that produce changes in the rod cells and/or cone cells, e.g., retinal degenerative diseases, color vision abnormalities, and so forth.

In the present Description, the "maximum activity wavelength" refers to the wavelength (λmax_act) of the irradiated light at which the photosensitive protein, said protein having a photosensitive channel activity, exhibits its maximum channel activity. Also, the "activity spectrum" in the present Description refers to the spectrum for the channel activity exhibited in the wavelength range of approximately 400 nm to 700 nm by the photosensitive protein having a photosensitive channel activity.

Typical and non-limiting specific examples of the disclosures of the Description are explained in detail below with reference to the drawings. These detailed explanations are aimed simply at showing preferred examples of the disclosures of the Description in detail so that they can be implemented by a person skilled in the art, and are not intended to limit the scope of the disclosures of the Description. The additional features and disclosures disclosed below may be used separately or together with other features and inventions to provide a further improved photoreceptor protein for visual color recognition, and a use thereof or the like.

The combinations of features and steps disclosed in the detailed explanations below are not essential for implementing the disclosures of the Description in the broadest sense, and are presented only for purposes of explaining typical examples of the disclosures of the Description in particular. Moreover, the various features of the typical examples above and below and the various features described in the independent and dependent claims do not have to be combined in the same way as in the specific examples described here, or in the listed order, when providing addition useful embodiments of the disclosures of the Description.

All features described in the Description and/or Claims are intended as individual and independent disclosures restricting the initial disclosures and the claimed matter specifying the invention, separately from the constitution of features described in the Examples and/or Claims. Moreover, all descriptions of numerical ranges and groups or sets are intended to include intermediate configurations for purposes of restricting the initial disclosures and the claimed matter specifying the invention.

(Mutants of the First Protein)

(1) The First Protein

The first protein has the amino sequence given by SEQ ID NO: 1 and is characterized by this amino acid sequence. The first protein is a protein composed of 367 amino acid residues having a DTD (aspartic acid-threonine-aspartic acid) motif that corresponds to the DTD motif of bacteriorhodopsin, which is a light-driven proton pump originating from halophilic archaeal, and the first protein has been found to have a low amino acid sequence identity with the cation channelrhodopsins 1 to 3 from *G. theta* that have been identified up to now (33%, 34%, and 39% versus each, respectively) (Biophysics and Pysicobiology. Vol. 14, pp. 57-66 (2017)). In addition, the first protein, as previously noted, is a protein originating from *G. theta* and has been identified by the present inventors as a photosensitive cation channelrhodopsin (ibid.). The first protein can transport both $Na^+$ and $H^+$ (ibid.).

The DTD motif in the first protein is D116, T120, and D127. The DTD motif in the light-driven proton pump bacteriorhodopsin is D85, T89, and D96 in the amino acid sequence. The first protein is provided with this DTD motif and additionally with K113, D242, and K246. These amino acids correspond to R82, D212, and K216 in the bacteriorhodopsin.

In addition, based, inter alia, on its amino acid sequence, the first protein is expected to be an ion channel protein that is constituted of seven-transmembrane helices. The first protein is provided with a region (extracellular region) constituting a moiety exposed on the extracellular side of the cell membrane or, located in the vicinity thereof, constituting the extracellular region of the ion channel; a region (gate region) located in the interior of the cell membrane and constituting the permeation pathway of the ion channel; and a region (cytoplasmic region) present on the cytoplasmic side of the cell membrane and constituting the ion channel cytoplasmic region.

The present inventors believe that, for example, the following amino acid residue positions or regions can be assigned to these regions in the first protein. Because the first protein has the DTD motif, it was thought that there would be a correlation in amino acid sequence and/or molecular structure with bacteriorhodopsin having the same DTD motif as described above (light-driven proton pump of halophilic archaeal origin). An ion permeation pathway in the interior of the first protein is therefore hypothesized based on the molecular structure of the known bacteriorhodopsin. Unless specifically indicated otherwise, in this Description the amino acid residue positions shown for the first protein refer to the positions in the amino acid sequence represented by SEQ ID NO: 1.

(Extracellular Region)

The extracellular region in the first protein is thought to be the following amino acid sequence regions: positions 1 to 41, positions 92 to 115, positions 147 to 165, and positions 222 to 237.

(Cytoplasmic Region)

The cytoplasmic region in the first protein is predicted to be the following amino acid sequence regions: positions 51 to 82, positions 125 to 138, positions 174 to 213, and positions 250 to 367.

(Gate Region)

The gate region in the first protein is presumed to be the following amino acid sequence regions: positions 42 to 50, positions 83 to 91, positions 116 to 124, positions 139 to 146, positions 166 to 173, positions 214 to 221, and positions 238 to 249.

(Channel Activity)

The first protein is a protein that has a photosensitive cation channel activity and that is also a light-driven proton pump, and, when it is expressed in the cell membrane, for example, a channel current is produced by the passage through the cell membrane of protons ($H^+$) and cations ($Na^+$) upon exposure to green light at 530 nm. The activity of channel current generation through exposure to light is generally called channel activity.

The channel activity of the first protein can be measured by a whole-cell patch clamp method when the first protein, for example, is expressed on a cell membrane of a suitable mammalian cell and then irradiated with light, for example, of a constant intensity having a maximum absorption wavelength of around 530 nm for a certain period of time. The mammalian cell is preferably not provided with another light-gated cation channel or light-driven proton pump. The whole-cell patch clamp method is a method that measures, as charge transfer (current), the total amount of ions that traverse the cell membrane for a single cell. The amount of channel current measured by this method can be regarded as channel activity.

The following method is provided as a specific example. Thus, DNA (mammalian codon usage as necessary) encoding the amino acid sequence of the first protein is synthesized; an insertion plasmid is prepared by its incorporation in a vector plasmid for use with mammalian cells, e.g., peGFP-N1, in such a way that eGFP is tagged at the C-terminal of the first protein and in such a way that the first protein is expressed at satisfactory levels; and transfection is carried out by introducing this plasmid into mammalian cells, e.g., ND/723 cells, using the lipofection method. Expression in the cell membrane of the recipient cells liar the first protein can be confirmed by the fluorescence of the eGFP.

For cells in which the first protein is transiently expressed on the cell membrane in this way, a patch clamp by whole cell recording is performed in a state where the first protein is stably expressed, for example, within 24 to 48 hours after transfection.

While the measurement conditions in the electrophysiological measurements using, e.g., the whole-cell patch clamp method, are not particularly limited, the following conditions can be adopted as an example.

TABLE 3

| | |
|---|---|
| (1) current amplifier | Axopatch 200B amp (Molecular Devices) |
| (2) analog/digital converter | Digidata 1550 or Digidata 1320 (Molecular Devices) |
| (3) software | control software: Clampex 10.0; analytic software: Clampfit 10.7 |
| (4) microscope | IX-73 or IX-70 (Olympus) |
| (5) pipette | glass pipette produced with a Micropipette Puller P-97 (Sutter Instrument) and fire-polished with an MF-830 (Narishige), pipette resistance: 1.5 to 2.5 MΩ |
| (6) extracellular solution | 140 mM NaCl, 2 mM $MgCl_2$, 2 mM $CaCl_2$, 2 mM KCl, 10 mM Hepes-NaOH, pH 7.2, |
| (7) intracellular solution | 110 mM NaCl, 2 mM $MgCl_2$, 1 mM $CaCl_2$, 5 mM KCl, 10 mM EGTA, 10 mM Hepes-NaOH, pH 7.2. |
| (8) current recording conditions | irradiated light: 530 nm ± 40 nm (preferably 530 nm ± 30 nm, more preferably 530 nm ± 20 nm, still more preferably 530 nm ± 10 nm, and even more preferably 530 nm ± 5 nm), light intensity: 6.9 $mW/mm^2$, irradiation time: 100 ms to 600 ms, recording time: 300 ms to 1000 ms, room temperature<br>The light intensity is always 0.1 $mW/mm^2$ in the measurement of the activity spectra. Current measurement is first carried out by irradiation with light at a wavelength of 410 nm. After this, light is irradiated at a wavelength on a 10 nm wavelength interval, e.g., 420 nm, 430 nm, and the current response is measured for each light irradiation. This is carried out in the wavelength range to 650 nm. The activity spectrum is constructed from the current values obtained for irradiation at each wavelength. The wavelength of the light yielding the maximum current value is defined as the maximum activity wavelength (λmax_act). |

The peak-form maximum current value (Ip) produced upon exposure of light to the cell and the current value (Is) provided by attenuation to a constant level during irradiation with light, as yielded by electrophysiological measurement by, e.g., the whole-cell patch clamp method, for example, using the conditions given above, can each be termed channel current values of the first protein. For example, either or both of the Ip and Is can be termed for the channel activity of the first protein. In the addition, dividing Is by Ip gives the channel opening ratio, described below.

The present mutant comprises an amino acid residue that is different from that in the first amino acid sequence of the first protein, at a position or positions corresponding to one or two or more positions in the first protein, and may be a protein obtained by artificially modifying the first protein, or may be a naturally occurring protein or a variant thereof. The first mutant is also applied to, for example, a protein having an amino acid sequence having a certain degree of identity with the first amino acid sequence. Thus, in addition to artificial proteins, and in a range in which a certain degree of identity with the first protein is exhibited, the first mutant may be a protein of natural origin, e.g., a cation ion channel, or a modification thereof, of microbial origin or originating with closely related algae in addition to algae that is the same source as the first protein. The concept of identity is described below.

Here, the position or positions corresponding to one or two or more positions in the first amino acid sequence, are the position or positions of the one or two or more amino acid residues in the first mutant that correspond to the one or two or more positions in the first amino acid sequence when the amino acid sequence of the present mutant is aligned with the first amino acid sequence. This alignment is synonymous with the alignment used when measuring the identity for amino acid sequences and base sequences, vide infra. For example, the position in the present mutant that corresponds to a position in the first amino acid sequence can be established by alignment using a known amino acid sequence alignment program, e.g., BLAST (https://blast.ncbi.nlm.nih.gov/Blast.cgi) or Pfam (http://pfam.xfam.org/), and using, for example, default parameters.

The first mutant can have a maximum activity wavelength or activity spectrum different from that of the first protein. The maximum activity wavelength of the first protein is approximately 520 nm. The maximum activity wavelength in the activity spectrum is established as follows: in the procedure for measuring the channel activity of the first protein, for example, light is irradiated at a wavelength on a prescribed wavelength interval, e.g., 10 nm, from the shorter wavelength side in the range of 400 nm to 700 nm for the wavelength of the irradiated light, for example, from 410 nm to 650 nm; the current response is measured for each light exposure: and the maximum activity wavelength is taken to be the wavelength of the light at which the maximum current value is obtained. The activity spectrum is constructed from the current values when the wavelength of the irradiated light is sequentially shifted from the shorter wavelength side to the longer wavelength side. The light intensity during measurement of the activity spectrum may be, for example, 0.1 mW/mm$^2$, and the light irradiation time may be 400 msec and the recording time may be 1 sec.

Various mutation sites in the first amino acid sequence for constructing the present mutant are described below.

Positions corresponding to one or two or more selections from the group consisting of the following sites in the first amino acid sequence are examples of mutation positions that provide the present mutant that contributes to color recognition at the retina: positions 53, 83, 87, 117, 120, 124, 137, 139, 142, 143, 146, 150, 169, 173, 177, 198, 204, 216, 217, 218, 231, 238, 245, and 247. The execution of an amino acid substitution mutation at these positions can bring about a shift in the maximum activity wavelength, to the shorter wavelength side or longer wavelength side, from the approximately 520 nm that is the maximum activity wavelength exhibited by the first protein, and can provide an activity spectrum that is different from that of the first protein.

Positions 147 and 151 in the first amino acid sequence are also examples.

The substitution modes at each mutation site are, for example, as follows.

- position 53: L53A, L53Y, L53N, L53M, L53L, L53I, L53C
- position 83: V83A, V83L, V83I, V83N, V83T, V83D, V83K
- position 87: A87S, A787K, A87S
- position 117: Y117A, Y117D, Y117F, Y117N
- position 120: T120S
- position 124: L124Q, L124C, L124T, L124A
- position 137: K137A, K137E, K137R, K13711, K137D, K137C
- position 139: T139A, A139D
- position 142: L142A
- position 143: F143A
- position 146: L146A, L146M, L1461, L146V, L146Y, L146C
- position 150: C150A
- position 169: G169S
- position 173: F173Y, F173A
- position 177: W177Y
- position 198: K198A, K198R, K1981-1, K198D, K198C
- position 204: K204A, K204E, K204R, K204H, K204D, K204C
- position 216: G216S, G216A, G216T, G216L, G216C, G216Y
- position 217: Y217F, Y217N
- position 218: P218A, P218T, P218S, P218G, P218C, P218H, P218N, P218V, P218D
- position 231: Q231L, Q231A, Q231D, Q231E, Q231T
- position 238: T238V
- position 245: A245M
- position 247: S247A, S247M
- position 147: T147C
- position 151: G151A Mutation Embodiment 1

Among these mutation sites, for example, one or two or more selections from the group consisting of positions 53, 83, 137, 146, 169, 177, 217, 218, and 247 tend to facilitate a shift in wavelength and/or tend to facilitate an improvement in channel activity. For example, positions 169, 177, 217, 218, and 247 are favorable for mutants that have a λmax_act, for example, less than 520 nm, for example, less than or equal to 515 nm, while positions 53, 83, 137, 146, and 218 are favorable for mutants that have a λmax_act greater than or equal to 530 nm.

For example, a mutation at position 53 tends to facilitate causing a shift in the maximum activity wavelength to the longer wavelength side. Such a substitution mode at position 53 can be exemplified by L53N and L53A.

For example, a mutation at position 83 tends to facilitate causing a shift in the maximum activity wavelength to the longer wavelength side. In addition, this mutation tends to facilitate improving the channel activity as a whole. Such a substitution mode at position 83 can be exemplified by V83A (λmax_act: 540 nm) and V83T.

For example, a mutation at position 137 tends to facilitate causing a shift in the maximum activity wavelength to the longer wavelength side. In addition, this mutation tends to facilitate improving the channel activity as a whole. A substitution mode at position 137 can be exemplified by K137A (λmax_act: 530 nm).

For example, a mutation at position 146 tends to facilitate causing a shift in the maximum activity wavelength to the longer wavelength side. In addition, this mutation tends to facilitate improving the channel activity as a whole. A substitution mode at position 146 can be exemplified by L146A (λmax_act: 530 nm).

For example, a mutation at position 169 tends to facilitate causing a shift in the maximum activity wavelength to the shorter wavelength side. A substitution mode at position 169 can be exemplified by G169S (λmax_act: 510 nm).

For example, a mutation at position 177 tends to facilitate causing a shift in the maximum activity wavelength to the shorter wavelength side. A substitution mode at position 177 can be exemplified by W177Y (λmax_act: 510 nm).

For example, a mutation at position 217 tends to facilitate causing a shift in the maximum activity wavelength to the shorter wavelength side. Substitution modes at position 217 can be exemplified by Y217F (λmax_act: 475 nm) and Y217N.

For example, a mutation at position 218 tends to facilitate causing a shift in the maximum activity wavelength to the longer wavelength side or the shorter wavelength side. In addition, this mutation tends to facilitate improving the channel activity as a whole. Substitution modes at position 218 can be exemplified by P218T (λmax_act: 510 nm), P218A (λmax_act: 530 nm), P218S, P218G, and P218C.

For example, a mutation at position 247 tends to facilitate causing a shift in the maximum activity wavelength to either the longer wavelength side or the shorter wavelength side. In addition, this mutation tends to facilitate improving the channel activity as a whole. Substitution modes at position 247 can be exemplified by S247A (λmax_act: 510 nm) and S247M (λmax_act: 530 nm).

Mutation Embodiment 2

Among the aforementioned mutation sites, for example, mutations at one or two or more selections from the group consisting of positions 137, 146, 150, 177, 198, 245, and 247, while providing a λmax_act of about at least 520 nm to less than 530 nm, are advantageous, for example, on the following points: the channel activity is high and a contribution is made to improving the channel activity when an additive mutant is executed with another mutation.

Mutation at position 137 can be exemplified by K137A: mutation at position 146 can be exemplified by 1.146A; mutation at position 150 can be exemplified by C150A; mutation at position 177 can be exemplified by W177Y; mutation at position 198 can be exemplified by K198A; mutation at position 245 can be exemplified by A245M; and mutation at position 247 can be exemplified by S247A and S247M.

Mutation Embodiment 3

Among the aforementioned mutation sites, for example, it has been discovered "for the first time" that one or two or more selections from the group consisting of positions 150, 169, 177, 218, and 247 are the positions of amino acid residues that interact with the retinal borne by the first protein, or are in the vicinity thereof, or are the positions of amino acid residues that influence the steric configuration of amino acid residues that interact with the retinal, and are favorable for acquiring a maximum activity wavelength or activity spectrum different from that of the first protein.

Mutation at position 150 can be exemplified by C150A; mutation at position 169 can be exemplified by G169S: mutation at position 177 can be exemplified by W177Y; mutation at position 198 can be exemplified by K198A: mutations at position 218 can be exemplified by P218A, P218S, P218G, and P218T; and mutations at position 247 can be exemplified by S247A and S247M.

Mutation Embodiment 4

Among the aforementioned mutation sites, for example, one or two or more selections from the group consisting of positions 87, 117, 120, 124, 139, 142, 143, 173, 204, 216, and 231 are thought to be the positions of gate region amino acid residues that interact with the retinal borne by the first protein, or positions in the vicinity thereof, and are favorable for acquiring a maximum activity wavelength or activity spectrum different from that of the first protein.

Mutations at position 87 can be exemplified by A87S, A787K, and A87S; mutations at position 117 can be exemplified by Y117A, Y117D, Y117F, and Y117N; mutation at position 120 can be exemplified by T120S; mutations at position 124 can be exemplified by L124C, L124T, and L124A; mutations at position 139 can be exemplified by T139A and T139D; mutation at position 142 can be exemplified by L142A; mutation at position 143 can be exemplified by F143A; mutations at position 173 can be exemplified by F173Y and F173A; mutations at position 204 can be exemplified by K204A and 1(204E; mutation at position 216 can be exemplified by G216S; and mutation at position 231 can be exemplified by Q231L.

For example, mutation at position 117 can contribute to shifting λmax_act to the shorter wavelength side of less than 520 nm. This mutation can be exemplified by Y117A, Y117F, and Y117N.

Mutation Embodiment 5

Among the aforementioned mutations, position 147 is located in the extracellular region in the vicinity of the gate region. This mutation can contribute to shifting to a λmax_act of less than 520 nm. It can also increase the channel activity itself. In addition, it can contribute to improving the channel activity when an additive mutant is executed with another mutation that is a mutation in the gate region and that participates in a wavelength shift to a λmax_act of less than 520 nm. T147C is an example of a substitution mode at position 147.

In addition, position 151 is located in the extracellular region in the vicinity of the gate region. This mutation can contribute to a λmax_act of less than 520 nm. It can also increase the channel activity itself. Moreover, it can contribute to improving the channel activity when an additive mutant is executed with another mutation that is a mutation in the gate region and that participates in a wavelength shift to a λmax_act of less than 520 nm. G151A is an example of a substitution mode at position 151.

For example, the combination of mutations at positions 147 and 151 can contribute to a shift in λmax_act to the shorter wavelength side of less than 520 nm and can also contribute to increasing the channel activity.

In addition, a mutation at position 147 and/or position 151, which are mutations in the extracellular region in the vicinity of the gate region, can be combined with a mutation at position 217, which is a mutation in the gate region that tends to facilitate bringing about a shift in λmax_act to the shorter wavelength side. This additive mutation can cause the λmax_act mediated by position 217 to shift to even shorter wavelengths. For example, the additive mutant in which T147C and G151A are combined with Y217F can bring about an additional shift in λmax_act from the 475 nm that is the maximum activity wavelength for Y217F.

When the channel activity is considered, the present mutant can be provided with a mutation selected from the gate region, e.g., positions 83, 87, 146, 216, and so forth. Suitable combinations can also be made with mutations in the cytoplasmic region, for example, positions 53, 76, 137, 198, and/or 204. Moreover, suitable combinations can be made with mutations at positions 230 and/231 in the extracellular region.

In a preferred embodiment of the present mutant, at least one mutation site is selected from the group consisting of positions 87, 117, 120, 124, 139, 142, 143, 146, 150, 169, 173, 177, 217, 218, 238, 245, and 247. Amino acid substitution modes at these mutation sites have already been described.

Based on the preceding discussion, it may be advantageous, for example, for the present mutant to have an amino acid substitution mutation at a mutation site as indicated below or for the present mutant to employ the following mutation modes at this mutation site.

TABLE 4

| position in first amino acid sequence | amino acid substitution mode | | | |
|---|---|---|---|---|
| 53 | L53N | | | |
| 83 | V83A | | | |
| 137 | K137A | | | |
| 146 | L146A | | | |
| 150 | C150A | | | |
| 169 | G169S | | | |
| 177 | W177Y | | | |
| 198 | K198A | | | |
| 217 | Y217F | Y217N | | |
| 218 | P218A | P218S | P218G | P218T |
| 238 | T238V | | | |
| 245 | A245M | | | |
| 247 | S247A | S247M | | |
| 146/150 | L146A/C150A | | | |
| 146/169 | L146A/G169S | | | |
| 146/177 | L146A/W177Y | | | |
| 146/217 | L146A/Y217F | | | |
| 147/218 | L146A/P218A | L146A/P218T | L146A/P218S | L146A/P218G |
| 146/238 | L146A/T238V | | | |
| 83/146/218 | V83A/L146A/P218A | | | |
| 147 | T147C | | | |
| 147/151 | T147C/G151A | | | |
| 147/151/217 | T147C/G151A/Y217F | | | |

TABLE 5

| position in first amino acid sequence | amino acid substitution mode | | | |
|---|---|---|---|---|
| 53 | L53A | | | |
| 83 | V83T | | | |
| 87 | A87S | | | |
| 117 | Y117A | Y117D | Y117F | Y117N |
| 124 | L124Q | L124C | L124T | L124A |
| 142 | L142A | | | |
| 204 | K204A | | | |
| 216 | G216S | | | |
| 231 | Q231L | | | |
| 137/204 | K137A/K204A | | | |
| 146/218 | L146A/P218C | L146A/P218H | L146A/P218N | L146A/P218V |

At least one mutation in the present mutant is preferably selected from the mutation modes given in Table 4 other than the L53N, V83A, K137A, and K198A mutation modes. In addition, at least one mutation in the present mutant is preferably selected from the mutation modes given in Table 5 other than the L53A, K204A, G549S, and Q231L mutation modes.

In addition to the positions indicated in the preceding, the present mutant may also be provided with substitution mutations of 1 to not more than 30, and for example not more than 25, for example not more than 20, for example not more than 15, for example not more than 10, and for example not more than several amino acid residues, or may also be provided with substitution mutations, deletion mutations, and/or insertion mutations of 1 to not more than 30, and for example not more than 25, for example not more than 20, for example not more than 15, for example not more than 10, and for example not more than several amino acid residues.

In addition to the above-described mutations for color recognition, the present mutant may also be provided with the various mutations as described in the following in the extracellular region, cytoplasmic region, and gate region. While the perspective for these mutation sites and mutation modes is based on improving the channel activity and/or the opening ratio, they may overlap with the mutation sites and mutation modes for color recognition.

(Mutations in Extracellular Region)

As noted above, the extracellular region is thought to be positions 1 to 41, 92 to 115, 147 to 165, and 222 to 237, and the mutation positions in this amino acid region can be exemplified by positions 39, 94, 98, 102, 110, 113, 114, 162, 224, and 225. Additional examples are positions 230, 231, and 235. Examples of the substitution mutation are D39N, R94M, R94K, R94Q, 1198A, D102N, N110L, K113A, K113N, Y114A, R162A. and S230E. Additional examples are T224A, E225A, E225Q, Q231L, H235A, H235N, and H235M.

(Mutations in Cytoplasmic Region)

As noted above, the cytoplasmic region is presumed to be positions 51 to 82, 125 to 138, 174 to 213, and 250 to 367, and the mutation positions in this amino acid region can be exemplified by positions 53, 61, 68, 74, 76, 80, 130, 137, 194, 195, and 198. Additional examples are positions 200, 204, 205, 209, 210, 253, and 254. Examples of the substitution mutations are K61A, R74A, E76Q, S80A, K137E, K137A, K198A, R200A, K204A. and K204E. Additional examples are L53A, L53N, E68Q, W130A, E194Q, D195N, L205A, L209A, Y210F, L253N, L253S, L254N, and L254S.

(Mutations in Gate Region)

As noted above, the gate region is presumed to be positions 42 to 50, 83 to 91, 116 to 124, 139 to 146, 166 to 173, 214 to 221, and 238 to 249, and the mutation positions in this amino acid region can be exemplified by positions 46, 83, 84, 87, 90, 91, 116, 117, 120, 124, 139, 142, 143, 146, and 173. Additional examples are positions 214, 216, 217, 238, 242, and 245. The substitution mutations can be exemplified by L46A, V83A, V83T, V83D, V83K, N84P, N84K, A87S, A87N, A87K, T90A, Y91A, D116A, D116T, Y117A, T120S, L124C, L124T, and L124A, Additional examples are T139A, T139D, L142A, F143A, L146A, F173A, F173Y, W214A, W214Y, G216S, Y217A, Y217F, Y217W, T238A, T238K, T238D, D242A and A242N, A245N, and L245S.

For example, mutations such as these can be exemplified by the substitution mutations given in the following Table 6. The substitution mutations given in Table 7 are also examples.

TABLE 6

| position in first amino acid sequence | mode of amino acid substitution |
|---|---|
| 39 | D39N |
| 46 | L46A |
| 53 | L53A, L53N |
| 61 | K61A |
| 68 | E68Q |
| 74 | R74A |
| 76 | E76Q |
| 80 | S80A |
| 83 | V83T, V83A, V83D, V83K |
| 84 | N84P, N84K |
| 87 | A87S, A87N, A87K |
| 90 | T90A |
| 91 | Y91A |
| 94 | R94M, R94K, R94Q |
| 98 | H98A |
| 102 | D102N |
| 110 | N110L |
| 113 | K113A, K113N |
| 114 | Y114A |

TABLE 6-continued

| position in first amino acid sequence | mode of amino acid substitution |
|---|---|
| 116 | D116A, D116T |
| 117 | Y117A |
| 120 | T120S |
| 124 | L124C, L124T, L124A |
| 130 | W130A |
| 137 | K137A, K137E |
| 139 | T139A, T139D |
| 142 | L142A |
| 143 | F143A |
| 146 | L146A |
| 162 | R162A |
| 173 | F173Y, F173A |
| 194 | E194Q |
| 195 | D195N |
| 198 | K198A |
| 200 | R200A |
| 204 | K204A, K204E |
| 205 | L205A |
| 209 | L209A |
| 210 | Y210F |
| 214 | W214A. W214Y |
| 216 | G216S |
| 217 | Y217A, Y217F, Y217W |
| 224 | T224A |
| 225 | E225A, E225Q |
| 230 | S230E |
| 231 | Q231L |
| 235 | H235N, H235A, H235M |
| 238 | T238A, T238K, T238D |
| 242 | D242A, D242N |
| 245 | A245N, A245S |
| 253 | L253N, L253S |
| 254 | L254N, L254S |

TABLE 7

| position in first amino acid sequence | mode of amino acid substitution |
|---|---|
| 76 | E76D, E76Q, E76N, E76A, E76T |
| 83 | V83A, V83L, V83I, V83T, V83N |
| 137 | K137A, K137R, K137H, K137D, K137C |
| 146 | L146A, L146M, L146I, L146V, L146Y, L146C |
| 198 | K198A, K198R, K198H, K198D, K198C |
| 204 | K204A, K204R, K204H, K204D, K204C |
| 231 | Q231L, Q231A, Q231D, Q231E, Q231T |
| 230 | S230E, S230T, S230Y, S230A |
| position in first amino acid sequence | mode of amino acid substitution |
| 53 | L53A, L53Y, L53, L53M, L53V, L53I, L53C |
| 216 | G216A, G216S, G216T, G216L, G216C, G216Y |

The present mutant is preferably provided with the DTD motif possessed by the first protein. That is, it is preferably provided with the amino acid residues (I), T, and D, respectively) at the positions corresponding to D116, T120, and D127 in the first amino acid sequence. In addition, the present mutant is preferably provided with this DTD motif and with amino acid residues corresponding to one or two or more selected from K113, D242, and K246 in the first amino acid sequence.

The identity of the present mutant with the first amino acid sequence is not particularly limited, but is, for example, 75% or more, for example, 80% or more, and for example, 85% or more, for example, 90% or more, and for example, 95% or more, and for example, 97% or more, for example, 98% or more, and for example, 99% or more, for example, 99.5% or more. The similarity is, for example, at least 80%, and for example at least 85%, for example at least 90%, for example at least 95%, for example at least 97%, for example at least 98%, for example at least 99%, and for example at least 99.5%.

In this Description, identity and similarity are known in the relevant field of art and are relationships between or among two or more proteins or two or more polynucleotides that are determined by sequence comparisons. In the concerned art, "identity" means the degree of sequence invariance between amino acid sequences or polynucleotide sequences, as determined by alignment between the amino acid sequences or polynucleotide sequences or, depending on the case, alignment among a series of such sequences. In addition, similarity means the degree of correlation between amino acid sequences or polynucleotide sequences, as determined by alignment between amino acid sequences or polynucleotide sequences or, depending on the case, by alignment among a series of partial sequences. More specifically, it is determined by the identity and conservation (substitution that retains a specific amino acid residue in a sequence or that maintains the physicochemical characteristics for a sequence) of sequences. Similarity is referred to as Similarity in the sequence homology search results of BLAST, described below. The method for determining the identity and similarity preferably is a method designed to provide the longest alignment between the sequences being compared. Methods for determining identity and similarity are provided in the form of publicly available programs. For example, the determination can be made using the BLAST (Basic Local Alignment Search Tool) program from Altschul et al. (for example, Altschul S F, Gish W. Miller W. Myers E W. Lipman D J., J. Mol. Biol., 215: p 403-410 (1990), Altschul S F, Madden T L, Schaffer A A, Zhang i, Miller W, Lipman D J., Nucleic Acids Res. 25: p 3389-3402 (1997)) or the alignment function of UniProtKB. The conditions in the case of use of software such as BLAST or UniProtKB are not particularly limited, but the use of default values is preferred.

The amino acid sequence alignment can be established using an amino acid sequence alignment program, e.g., BLAST (https://blast.ncbi.nlm.nih.gov/Blast.cgi), and performing the alignment using, for example, the default parameters.

(The Maximum Activity Wavelength λmax_act of the Present Mutant, Etc.)

For example, as shown in FIG. 1, the present mutant can have various maximum activity wavelengths. It can be used—in correspondence, inter alia, to the maximum activity wavelength λmax_act of the present mutant—as the S cone, M cone, or L cone that is expressed in human cone cells. The maximum activity wavelength substituting for the respective cone is established as appropriate; for example, when it is 400 nm to 515 nm, for example, use as a human S cone, which has its sensitivity peak at short wavelengths, is possible. In addition, when, for example, the maximum activity wavelength λmax_act of the present mutant is from 515 nm to 545 nm, for example, use as an M cone is possible. In addition, when, for example, the maximum activity wavelength λmax_act is from 540 nm to 600 nm, for example, use as an L cone is possible.

When the maximum activity wavelength of the present mutant is shifted to the shorter wavelength side or longer wavelength side relative to the first protein, the present mutant can then be regarded as having an activity spectrum different from that of the first protein. In addition, even when the maximum activity wavelength of the present mutant is equal to that of the first protein, the activity spectrum can still be regarded as different from that of the first protein, for example, when a shoulder peak is present in the activity spectrum in the vicinity of the peak, or when the peak in the activity spectrum of the first protein is sharper (peak width is narrower), and so forth.

For example, the activity spectra can be compared between present mutants, and the activity spectra can be compared between the present mutant and the first protein, based on a first ratio, this being the ratio of a value corresponding to a channel activity at 440 nm relative to the value corresponding to the channel activity at the maximum activity wavelength of the present mutant, and on a second ratio, this being the ratio of a value corresponding to a channel activity at 600 nm relative to the value corresponding to the channel activity at the maximum activity wavelength.

The first protein has a first ratio of 0.3, a second ratio of approximately 0.18, a first ratio/second ratio of 1.67, and a second ratio/first ratio of 0.6; however, when the first ratio is about at least 2-times the second ratio, the trend occurs for the maximum activity wavelength λmax_act to be shifted to the shorter wavelength side from that of the first protein. When the first ratio is additionally at least 3-times larger, for example, at least 4-times larger than the second ratio, the trends occurs of an even larger shift to the shorter wavelength side. When the first ratio is for example at least 0.4, for example at least 0.5, for example at least 0.6, for example at least 0.7, or for example at least 0.8, the trend of having the maximum activity wavelength on the shorter wavelength side becomes pronounced and, inter alia, a shoulder peak may also be present on the shorter wavelength side of the maximum activity wavelength λmax_act.

When, on the other hand, the second ratio is, for example at least 0.7-times, for example at least 0.8-times, for example at least 0.9-times, for example at least 1.0-times, for example at least 1.1-times, for example at least 1.2-times, for example at least 1.3 times, or for example at least 1.4-times the first ratio, the trend occurs for the maximum activity wavelength λmax_act to then be shifted to the longer wavelength side from that of the first protein. In addition, for example, when the second ratio is for example at least 0.3, for example at least 0.4, for example at least 0.5, for example at least 0.6, for example at least 0.7, for example at least 0.8, or for example at least 0.9, the trend of having the maximum activity wavelength on the shorter wavelength side becomes pronounced and, inter alia, a shoulder peak may also be present on the longer wavelength side of the maximum activity wavelength λmax_act.

The color responsiveness of the first mutant can be characterized by the first ratio and second ratio, which regulate the maximum activity wavelength λmax_act and the activity spectrum.

The present mutant has a channel activity. The channel activity can be checked using the same method as described for the first protein. The present mutant preferably has at least a certain channel activity. For example, when measured using the already described method for evaluating channel activity and electrophysiological recording conditions (irradiation time of 400 ms), pA/pF preferably is at least 30, for example, preferably at least 40.

In addition, the present mutant, while having a channel activity, has a channel activity at the maximum activity wavelength, in accordance with the above-described method, for example, that is at least 30%, for example at least 40%, for example at least 50%, for example at least 60%, for example at least 70%, for example at least 80%, for example at least 90%, or for example at least 100% of the channel activity pA/pF exhibited by the first protein.

The present mutant also preferably has at least a certain channel opening ratio. For example, when measured using the already described method for evaluating channel activity and electrophysiological recording conditions (irradiation time of 400 ms), the channel opening ratio (Is/Ip) preferably is for example at least 0.7, for example at least 0.8, for example at least 0.85, for example at least 0.9, for example at least 0.95, for example at least 0.97, for example at least 0.98, or for example at least 0.99.

The channel opening ratio of the present mutant can also be measured as for the first protein. Using 100% for the opening ratio (Is/Ip) of the first protein, the channel opening ratio of the present mutant, while not being particularly limited, is for example 30%, for example at least 40%, for example at least 50%, for example at least 60%, for example at least 70%, for example at least 80%, for example at least 90%, or for example at least 100% of that of the first protein.

A person skilled in the art can obtain the present mutant having the intended maximum activity wavelength and/or activity spectrum and so forth by producing and evaluating various mutants and additive forms based on the mutation positions and favorable examples of substitution disclosed for the present mutant in this Description.

A person skilled in the art can carry out, for example, the fusion of various proteins to the N-terminal and/or C-terminal of the first protein and the present mutant.

A person skilled in the art can acquire the present mutant, for example, by acquiring a modified DNA by modification—using conventional mutagenesis methods, site-specific mutagenesis methods, a molecular evolution method using error-prone PCR, and so forth—of DNA (SEQ ID NO: 2) encoding the amino acid sequence of the first protein, and acquiring the first mutant based on, for example, this modified DNA. The procedure for acquiring the modified DNA can be exemplified by known methods, e.g., the Kunkel method or gapped duplex method, or methods based on these; for example, mutation can be introduced using a commercially available mutation introduction kit that utilizes any of various site-specific mutagenesis methods.

For example, the present mutant can be obtained as follows: a host, e.g., *P. pastoris,* is transfected using a DNA construct containing the thusly obtained modified DNA; this transfected cell is cultured according to a conventional method known to a person skilled in the art; and the present mutant is recovered from the cultured cell or the culture medium. For example, the present mutant can be isolated using a combination of conventional purification techniques. These techniques encompass, for example, ammonium sulfate fractionation, treatment with organic solvent, centrifugal separation, ultrafiltration, various types of chromatography (for example, gel filtration chromatography, ion-exchange chromatography, affinity chromatography, hydrophobic interaction chromatography, and so forth), high-performance liquid chromatography (H PLC), electrophoresis, and so forth.

Besides the preceding, the protein may also be obtained by introducing the modified DNA fused with DNA encoding a signal protein, e.g., GFP, into mammalian nerve cells such as ND7/23 cells, and inducing expression in the cell membrane.

(Polynucleotide)

The polynucleotide disclosed in this Description (also referred to hereafter simply as the present polynucleotide) can encode an amino acid sequence for the present mutant. Various forms can be adopted for this polynucleotide, but the region coding for this amino acid sequence is DNA or RNA and is typically DNA.

DNA fragments, RNA fragments, and various known forms adapted for, e.g., transfection, e.g., plasmids, vectors, and so forth, can be adopted for the present polynucleotide.

The present polynucleotide can be obtained by artificial synthesis in the form of DNA for obtaining the herein-described mutant, and in addition, as already described, can be acquired in the form of DNA based on the already described methods for acquiring mutants.

(Vector)

The vector disclosed in this Description (also referred to hereafter as the present vector) can be provided with the present polynucleotide. The purpose of the present vector is to bring about the expression of the present mutant in a host cell. Various forms can be adopted for the expression vector in conformity with, for example, the purpose and type of cell to be transfected.

For example, the addition of a suitable regulatory sequence and/or targeting sequence may be applied as appropriate with the present polynucleotide, and/or a codon usage frequency preferred for the selected host may be applied as appropriate for the coding sequence with the present polynucleotide. For example, the targeting sequence may be a targeting sequence that can encode an N-terminal or C-terminal extension that targets a light-gated ion channel to a prescribed site or compartment within the cell, e.g., cell membrane, synapse, postsynaptic site, or axon hillock, or endoplasmic reticulum, and so forth. A person skilled in the art can readily construct such a vector based on the well-known art available at the time of filing of the present application.

Methods for acquiring vectors for expressing the present mutant, and their constituent components, are well known to a person skilled in the art in the field of use of GFP and in the field of genetic engineering. For example, implementation can be carried by a person skilled in the art with reference as appropriate to, for example, the experimental manuals of T. Maniatis, J. Sambrook, et al. (Molecular Cloning, A Laboratory Manual, Cold Spring Harbor Laboratory. 1982, 1989, 2001).

The vector disclosed in the present Description is used, for example, according to the following modalities in the case of use, for example, to improve or regenerate vision (color vision) through the recovery of photosensitivity for color recognition in retinal nerve cells.

The present vector can be suitable for the gene therapy of eye diseases. It can be utilized in particular for virus-mediated gene delivery. The "virus-mediated gene delivery" means that the present vector can be packed in a virus and, as a result, can be delivered to a target region or cell. The following are examples of viruses suitable for gene therapy: retroviruses, adenoviruses, adeno-associated viruses, lentiviruses, poxviruses, alphaviruses, rabies viruses, Semliki Forest fever viruses, and herpes viruses. Gene therapy also includes non-viral methods such as the application of naked DNA, lipoplexes and polyplexes, and dendrimers.

For example, a known vector already used with the goal of visual function regeneration by the introduction of a gene encoding a protein for such treatment purposes, can be used as the present vector directed to eye diseases. For example, an AAV-2 viral vector can be used, and, for example, a CAG promoter, human gap junctional protein (connexin-36) promoter (Greenberg K P et al., 2007. In vivo Transgene Expression in ON-Type Retinal Ganglion Cells: Applications to Retinal Disease. ARVO abstract, 2007), or mGluR6 promoter can be used as the promoter.

A particular type of retinal nerve cell can be targeted using a cell-specific promoter. The Pcp2(L7) promoter (Tomomura, M et al., 2001. Eur J Neurosci. 14:57-63) is a promoter than can target rod bipolar cells. The length of the active promoter is less than 2.5 Kb and due to this it can be packaged in the AAV virus cassette.

(Target Cell Transfection and Transfected Cells)

The transfected cell disclosed in this Description (also referred to as the present transfected cell in the following) retains the present polynucleotide capable of expressing the present mutant. The present transfected cell can be obtained by the introduction, into a target cell, of the already described present vector or the present polynucleotide as naked DNA. The method of introduction into the target cell can be exemplified by various heretofore known methods, for example, the calcium phosphate method, transfection method, transfection method, fusion method, protoplast method, electroporation method, lipofection method, lithium acetate method, and other methods.

As noted above, the transfected cell may also be provided by the introduction of the present nucleotide into a cell using a virus. Depending upon its method of production and its application, the transfected cell may be an in vitro cell or may be an in vivo cell, or may be produced in vitro and transplanted in vivo. Target cells for the transfected cell are described below.

(Use of Present Protein, Present Polynucleotide, Present Vector, and Present Transfected Cell for, inter alia, Vision Regeneration)

The present protein, present polynucleotide, present vector, and present transfected cell (also referred to below as the present protein and so forth) can be used, for example, to improve visual impairment including color vision abnormalities or regenerate visual function. That is, all of these can be used for optogenetic applications and research in order to prevent or treat eye diseases. While this is not a particular limitation, retinal photosensitivity can be improved or recovered by a gene therapy directed to bringing about the expression of the present mutant in, for example, prescribed retinal cells or nerve cells that are nonretinal cells in the vicinity of the retina. These cells can be provided with photosensitivity and this can bring about an improvement in vision or a regeneration of vision.

In this Description, visual impairment and eye diseases can be exemplified by retinitis pigmentosa, age-related macular degeneration, retinal detachment, diabetic retinopathy, retinal vein occlusion, glaucoma, color vision abnormalities, and so forth. Retinitis pigmentosa and age-related macular degeneration are preferred examples. In this Description, treatment refers to the effort—directed against a condition in which retinal function has been lost due to, for example, cell degeneration, death, or shedding—to improve or recover visual function including color vision or inhibit symptom progression by bringing about the improvement or recovery of the photosensitivity of, e.g., nerve cells and so forth for color recognition. In this Description, prevention refers to the effort—under circumstances in which there is an elevated possibility of the progression of cell degeneration, death, or shedding or in which there is an elevated risk of the onset of visual impairment—to improve or recover nerve cell photosensitivity and prevent loss of function or slow the onset of visual impairment. The "drug for the treatment or prevention of visual impairment, comprising a protein or a polynucleotide that encodes the described protein" as disclosed in the present Description, includes those used for such gene therapy. For example, the drug may be provided in the form of a vector for expressing the protein in a target tissue. In this case, the use is preferred of an expression vector that exhibits an excellent cell insertion efficiency, an excellent retention of intracellular replication, an excellent stability, an excellent expression efficiency, and so forth. Examples of such a vector include, but are not limited to, viral vectors such as adeno-associated virus vectors, retrovirus vectors, lentivirus vectors, (autonomously replicating) plasmids, transposons, and so forth. The protein expression vector according to the present invention is produced, for example, according to the methods described by Tomita H et al., Invest Ophthalmol Vis Sci. 2007 August; 48(8):3821-6, and Sugano E et al., Invest Ophthalmol Vis Sci. 2005 September; 46(9):3341-8, and gene introduction can be carried out into, for example, cells of a target tissue. In addition, the present mutant and so forth are also used for research purposes for, for example, such visual regeneration as well as optogenetics.

The present vector directed to the treatment of eye diseases, e.g., regeneration of vision, can be constituted so as to target all types of ganglion cells (both ON and OFF ganglion cells) or all types of bipolar cells (rod bipolar cells and ON and OFF cone bipolar cells).

Accordingly, this Description provides a drug composition for the treatment or prevention of visual impairments, wherein the drug composition contains the present mutant and so forth. The visual impairments can be exemplified by retinitis pigmentosa, age-related macular degeneration, retinal detachment, diabetic retinopathy, retinal vein occlusion, glaucoma, and color vision abnormalities, although there is no particular limitation to this.

Gene therapy using DNA encoding a photosensitive protein is known, and the present protein and so forth can also be used for gene therapy and research applications for eye diseases based on the same methods or relevant methods.

(Utilization of Present Mutant and so Forth for Optogenetics)

Using optogenetics, the present mutant and so forth are also useful for research applications concerning various neural pathways and for application to the treatment, etc. of neurological diseases. An intracellular-versus-extracellular potential difference (voltage difference) is generally present with nerve cells. In the normal state (during inhibition), the electrical membrane potential is about −70 mV to −80 mV relative to the cell exterior. This state is called hyperpolarization. Nerve cell activation (or firing, excitation) is triggered by the activation of voltage-sensitive sodium channels when the potential difference across the cell membrane rises to −40 mV to −20 mV (referred to as depolarization). The first protein is a photosensitive cation channel, and as a consequence, when expressed in the nerve cell membrane, it produces a channel current through the permeation of cations in association with exposure to light. This results in depolarization of the cell membrane, and as a result, nerve cell activation (firing, excitation) can be induced.

Accordingly, for example, a nerve cell serving as the target cell may be transfected using the present vector, or using a virus that incorporates the present vector, to bring about expression of the present mutant by the target cell. A channel current may then be produced upon exposure of the thusly transfected nerve cell to light. Through the in vitro preparation of the thusly transfected nerve cell and its transplantation into an organism, or through the transfection of a nerve cell in an organism using. e.g., the present vector, neural pathways that are activated in response to light irradiation from the exterior can be constructed within the organism. In particular, a present mutant having a maximum activity wavelength λmax_act on the longer wavelength side, due to its high tissue permeability, is favorable for optogenetic applications.

Accordingly, there is provided a method of use, comprising using a protein according to the present Description. or a polynucleotide that encodes said protein, to cause the firing of a muscle cell, cerebral epithelial neuron, or hippocampal neuron upon irradiation with light, for example, blue light (430 to 440 nm).

(Target Cells)

Target cells for obtaining transfected cells can be exemplified by yeast such as Saccharomyces cerevisiae, *Schizo-saccharo-myces pombe*, and *Pichia pastoris.*

Mammalian cells and insect cells are examples of other target cells. The mammalian cells can be exemplified, using an episomal vector for transient expression therein, by melanoma cells (for example, the BLM cell line), COS cells (produced by "African green monkey kidney CV1" cell infection), HEK cells ("human embryonic kidney cells", for example, HEK 293 cells), and BHK cells ("baby hamster kidney cells"), and otherwise can be exemplified by CHO cells ("Chinese hamster ovary cells"), myeloma cells, and MDCK cells ("Madin-Darby canine kidney cells"). The insect cells can be exemplified by baculovirus-infected Sf9 insect cells.

Considered from the standpoint of, e.g., the regeneration of vision, target cells for obtaining photosensitivity can be exemplified by mammalian cells such as photoreceptor cells, retinal rod cells, retinal cone cells, retinal ganglion cells, bipolar neurons, ganglion cells, pseudounipolar neurons, multipolar neurons, pyramidal neurons. Purkinje cells, and granule cells.

Viewed from the standpoint of, inter alia, optogenetics, the target cell can be exemplified by animal cells including mammalian cells. The mammalian cells can be exemplified by the use of neuroblastoma cells (for example, NG108-15 cells), melanoma cells (for example, the BLM cell line), COS cells (produced from "African green monkey kidney CV1 cells"), HEK cells ("human embryonic kidney cells", for example, HEK 293 cells), and BHK cells ("baby hamster kidney cells"), and otherwise can be exemplified by CHO cells ("Chinese hamster ovary cells"), myeloma cells, and MDCK cells ("Madin-Darby canine kidney cells"). Use with baculovirus-infected Sf9 insect cells is also possible.

The mammalian cells can also be exemplified by electrically excitable cells. Examples are hippocampal cells, bipolar nerve cells, ganglion cells, pseudounipolar nerve cells, multipolar nerve cells, pyramidal nerve cells. Purkinje cells, and granule cells. Electrically excitable cells include various nerve cells, e.g., sensory nerve cells that respond to contact, sound, light, and many other stimuli that can affect the cells of sensory organs; motor neurons that, receiving a signal from the brain or spinal cord, can trigger muscle contraction or exercise an influence on a gland; and interneurons that interconnect nerve cells within the same region of the brain or spinal cord. Additional examples are myocardium, smooth muscle, and skeletal muscle.

The target cells can also be exemplified by the cells, tissues, and organs in an animal, and by fertilized eggs, ES cells, and iPS cells capable of ultimately producing an animal or a part thereof. The animal can be exemplified by flies, nematodes, mice, rats, and monkeys. The thusly acquired results are, for example, such a transfected animal or a portion thereof.

The target cells which are transfected can be isolated (and genetically modified) and maintained and can be cultured at an appropriate temperature with an appropriate gas mixture (typically 37° C. 5% $CO_2$), optionally in a cell incubator, which is exemplified for specific cell lines or cell types in the examples and is known to a person skilled in the art. The culture conditions can vary with the individual cell type, and changes in conditions for a particular cell type can result in different phenotypes. Aside from the temperature and gas mixture, the growth medium is the factor that most generally varies among cell culture systems. The composition for a growth medium can vary with regard to pH, glucose concentration, and growth factors, and particularly with regard to the presence of other nutrient components. A commercially available growth medium may be used, or a growth medium can be prepared according to a composition available from the American Type Culture Collection (ATCC). The growth factors used in supplemented media are often derived from animal blood, such as fetal bovine serum. Antibiotics may also be added to the growth medium. Medium exchange and cell passage are among the common operations performed on cultured cells.

(Methods that Impart Photosensitivity to Nerve Cells)

The present mutant and so forth can impart photosensitivity to nerve cells. As a consequence, this method can be carried out as a method for improving visual impairment or a method for regenerating visual function, or can be applied in optogenetics to induce action potential of neurons. For example, by introducing a protein or polynucleotide that imparts photosensitivity into nerve cells present in a region thought to be involved with aggressiveness or memory formation in the mouse hippocampus, it can be ascertained whether and how the particular region is actually involved with aggressiveness or memory formation (Lin, D et al., 2011. Nature 470 (7333): 221-6 and OKUYAMA et al., 2016, Science (6307) 1536-1541).

In addition, for example, photosensitivity can be imparted to central or peripheral nerve cells in a human or a nonhuman animal and a channel current can then be produced by exposure to light of prescribed wavelength and intensity. This, as a consequence, makes it possible to activate the nerve cells and thereby ascertain whether activation or inhibition of nerve cells in a particular region contributes to a particular disease. In addition, the activation of nerve cells in this manner can support the recovery of central or peripheral neural pathways and can treat, for example, neurodegenerative diseases.

(Photoresponsive Cells)

The aforementioned target cells to which photosensitivity for color recognition has been conferred are provided in accordance with this Description as novel photosensitive cells (photosensitive material). These photosensitive cells can be used, for example, in the field of optogenetics in research related to, for example, the activation of neural activities.

(Screening Method)

The screening method disclosed in this Description can be provided with a step of evaluating a relationship between the irradiation wavelength of irradiated light and a channel activity for a test protein that is provided with an amino acid residue different from that in the first amino acid sequence represented by SEQ ID NO: 1, at a position or positions corresponding to one or two more positions in the first amino acid sequence. This screening method enables the acquisition of mutants that originate from the first protein and are provided with a channel activity for color recognition. The channel activity referenced here can be measured, for example, by the electrophysiological measurement method described above. Any, or a combination of two or more, of the Ip, Is, and channel opening ratio that have been described above can be adopted for the channel activity.

The mutant that is the test protein used in these screening methods can be obtained based on the mutant production methods described above. The embodiments and modes already described above can also be used in the evaluation of the channel activity.

EXAMPLES

Examples are described in the following as specific examples in order to more specifically describe the disclosure according to this Description. The following examples are examples in order to describe the disclosure according to this Description and do not limit its scope.

Then, ND7/23 cells, of mouse blastoma×rat nerve origin, i.e., mouse nerve/rat dorsal root ganglia origin, were cultured at 37° C. in a $CO_2$ incubator using DMEM (high glucose)+5% FBS culture medium. Using the vector prepared, the plasmid DNA was introduced into the ND7/23 cells using the lipofection method (Lipofectamine 2000, Thermo Fischer Scientific Inc.). Expression of the GtCCR4 mutant by the ND7/23 cells was confirmed by eGFP fluorescence.

Electrophysiological measurements by the whole-cell patch clamp method were performed using the following conditions at within 24 to 48 hours after gene insertion.

TABLE 8

| | |
|---|---|
| (1) current amplifier | Axopatch 200B amp (Molecular Devices) |
| (2) analog/digital converter | Digidata 1550 or Digidata 1320 (Molecular Devices) |
| (3) software | control software: Clampex 10.0; analytic software: Clampfit 10.7 |
| (4) microscope | IX-73 or IX-70 (Olympus) |
| (5) pipette | glass pipette produced with a Micropipette Puller P-97 (Sutter Instrument) and fire-polished with an MF-830 (Narishige), pipette resistance: 1.5 to 2.5 MΩ |
| (6) extracellular solution | 140 mM NaCl, 2 mM $MgCl_2$, 2 mM $CaCl_2$, 2 mM KCl, 10 mM Hepes-NaOH, pH 7.2, |
| (7) intracellular solution | 110 mM NaCl, 2 mM $MgCl_2$, 1 mM $CaCl_2$, 5 mM KCl, 10 mM EGTA, 10 mM Hepes-NaOH, pH 7.2. |
| (8) current recording conditions | irradiated light: 410 nm to 650 nm, light intensity: 0.1 mW/mm$^2$, irradiation time: 400 ms, recording time: 1000 ms, room temperature |
| (9) light source | OSG (Hamamatsu Photonics) |

Example 1

(Preparation of Vectors Containing DNA Encoding GtCCR4 Mutants, ND7/23 Transfection, and Electrophysiological Measurements on Transfected Cells (1))

Figure 2:
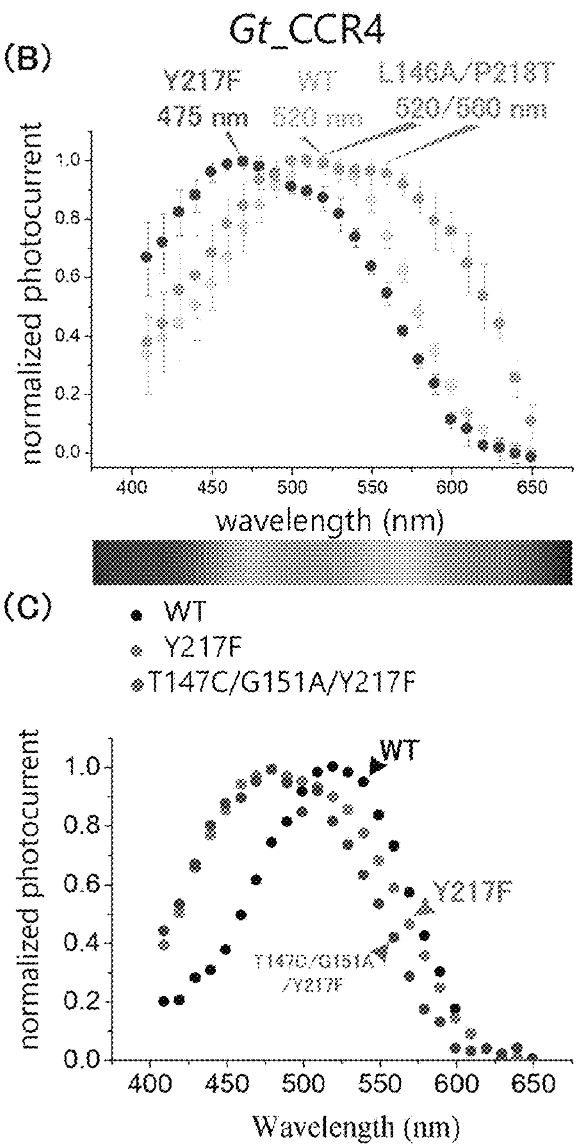
FIG. 2 is a diagram that combines the following: a diagram (A) giving the maximum activity wavelengths (λmax_act) of the mutants produced in the examples, a diagram (B) showing the activity spectra of Gt_CCR4 wild-type (WT), the Y217F mutant, and the Y146A/P218T mutant, and a diagram (C) showing the activity spectra of WT, the Y217F mutant, and the T147C/G151A/Y217F mutant.

Mutants provided with various single mutations or multiple mutations were designed based on the amino acid sequence (SEQ ID NO: 1) of GtCCR4. The base sequences encoding these were determined using the previously indicated codon usage, and preparation was carried out using the QuickChange method (QuikChange Site-Directed Mutagenesis Kit, Agilent Technologies, Inc). FIG. 2 shows the type of substitution mutations in the mutants.

Each of the DNA fragments was amplified using the primers indicated below. In addition, the vector DNA (pEGFP-N1) was also amplified using inverse PCR, pEGFP-GtCCR4 mutants incorporating each particular DNA fragment were fabricated by the In-Fusion reaction of the respective amplified DNA fragment and vector DNA fragment.

Primers for acquisition of DNA fragments (coding mutants originating from GtCCR4) forward primer: 5'CGAGCTCAAGCTTATGATGACAACAAGCGCCCCTAG3' (SEQ ID NO: 3)

reverse primer: 5'GACCGGTGGATCCTGAACAGCCTCAGACTCTTGCA3' (SEQ ID NO: 4)

Primers for acquisition of the vector fragment of vector pEGFP-N1 forward primer: 5'CATAAGCTTGAGCTCGAGATC3' (SEQ ID NO: 5)

reverse primer: 5'CAGGATCCACCGGTCGCCACC3' (SEQ ID NO: 6)

In the electrophysiological measurements, the wavelength dependence (activity spectrum) and maximum activity wavelength λmax_act were measured on each mutant by measuring the current response while varying the wavelength of the irradiated light.

(Measurement of the Activity Spectrum and Maximum Activity Wavelength)

For the measurement of the wavelength dependence (activity spectrum), a light intensity of 0.1 mW/mm$^2$ was always used for the irradiated light; the current was first measured for irradiation with light at a wavelength of 410 nm; and subsequent to this irradiation was performed using light at a wavelength longer by 10 nm each time and the current response under each irradiation was measured. This was performed in the wavelength range to 650 nm. The activity spectrum was constructed using the stationary current value (1s) obtained during irradiation at each wavelength. The maximum activity wavelength λmax_act was taken to be the wavelength of the light at which the maximum current value was obtained. The maximum activity wavelength λmax_act for each mutant is also given in FIG. 2. FIG. 2 additionally gives the individual activity spectra for the wild-type (WT) and mutants (Y117A, Y117F, Y117N, Y217F, L146A/P218T, and T147C/G151A/Y217F).

(Evaluation of the Photosensitivity in the Blue Region and Red Region)

Considering the results for the activity spectra obtained in the experiment described above, the blue region sensitivity was defined as the relative value (ratio) of the current value for irradiation with light at 440 nm to the current value at the maximum activity wavelength, and the red region sensitivity was defined as the relative value (ratio) of the current value for irradiation with light at 600 nm to the current value at the maximum activity wavelength. These results are given in FIG. 3 and FIG. 4.

As shown in FIG. 2(A), the individual mutants exhibited various maximum activity wavelengths λmax_act in accordance with the mutation mode. Among these. Y117A, Y117F, Y117N, G169S, W177Y, Y217F, Y218T, S247A, and L146A/Y217F brought about a shift in the maximum activity wavelength to the shorter wavelength side and an improved sensitivity in the blue region was thus confirmed. In addition, L53N, V83A, L146A/P218T, and V83A/L146A/P218T brought about a shift in the maximum activity wavelength to the longer wavelength side and an improved sensitivity in the red region was thus confirmed. L146A itself had a maximum activity wavelength of 530 nm, but was found to be advantageous in combination with other mutations.

In addition, as shown in FIG. 2(B) and FIG. 2(C), it was found that Y217F, L146A/P218T, and T147C/G151A/Y217F could all be candidates for novel visual pigments. Moreover, as shown in FIG. 2(C), T147C/G151A/Y217F was found to be a mutant that had a maximum activity wavelength furthest on the shorter wavelength side from Y217F. while its sensitivity on its longer wavelength sharply declined, and it could respond with a higher sensitivity on the shorter wavelength side.

Figure 3:
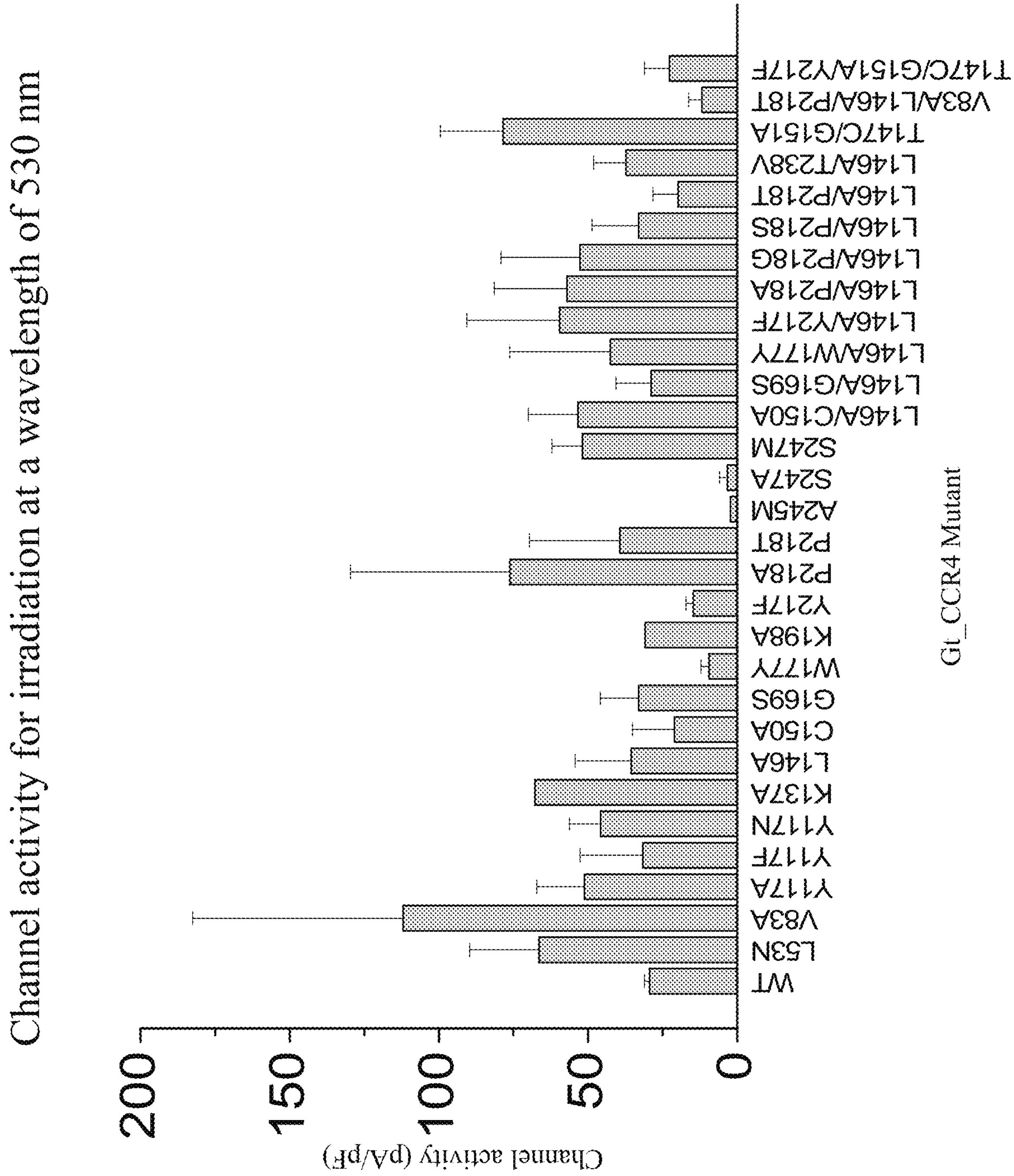
FIG. 3 is a diagram that shows a comparison of the results for the channel activity for irradiation at a wavelength of 530 nm for the mutants obtained in the examples.
Figure 4:
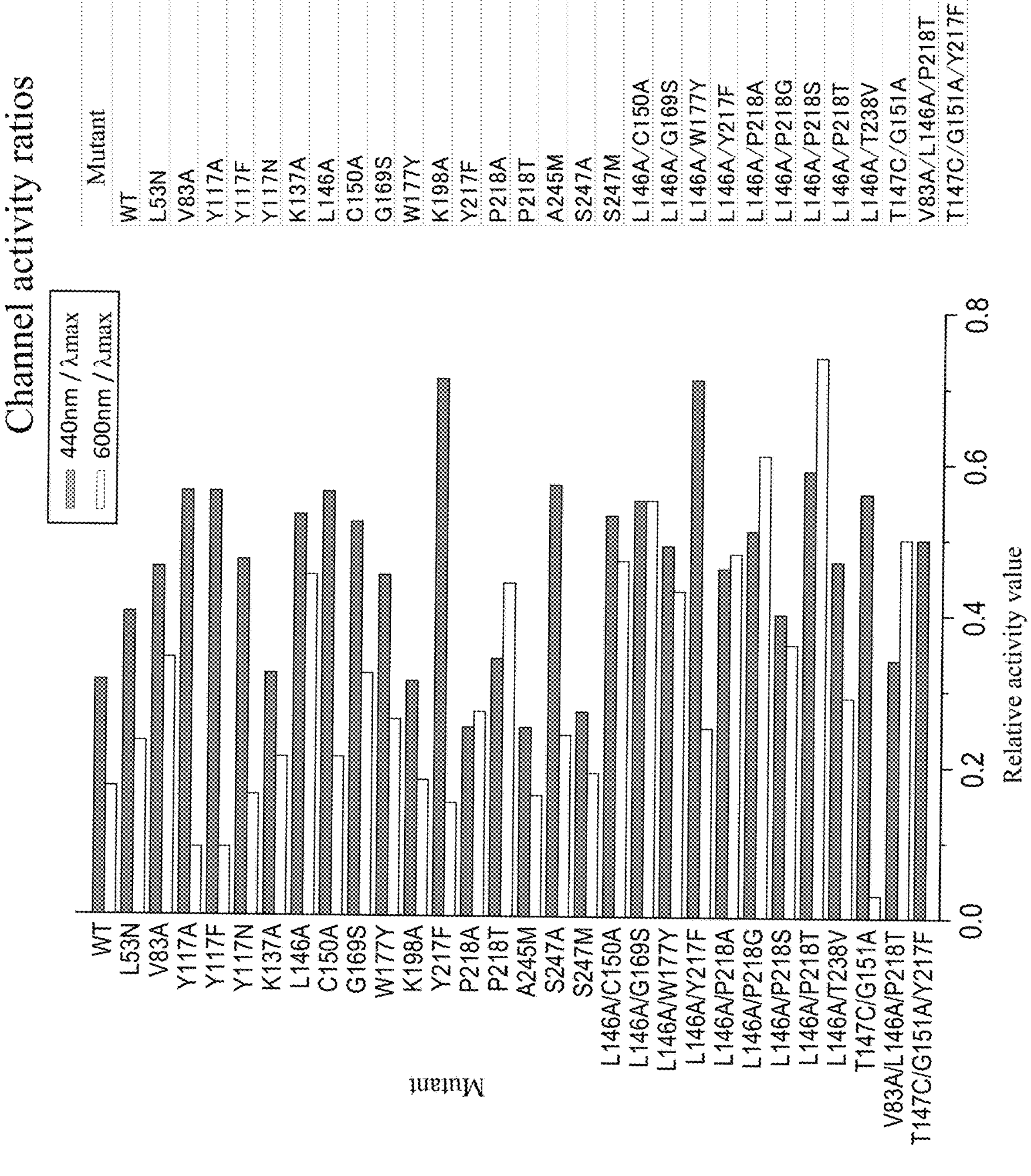
FIG. 4 is a diagram that shows the following: a comparison of the results for the channel activity for irradiation at a wavelength of 530 nm for the mutants obtained in the examples, and, for the mutants obtained in the examples, the ratio of the channel activity at λmax for the individual mutant with respect to the channel activity at 440 nm and the ratio of the channel activity at λmax for the individual mutant with respect to the channel activity at 660 nm.

As shown in FIG. 3 and FIG. 4, C150A, G169S, W177Y, Y217F, S247A, and L146A/Y217F were mutants that had large relative values for the current for irradiation with light at 440 nm, and these relative values for them were at least 0.4 and were at least 2-times larger than the relative value for irradiation with light at 600 nm. On the other hand. V83A. L146A, P218T, L146A/C150A, L146A/G169S, L146A/W177Y, L146A/P218A, L146A/P218G, L146A/P218T, and V83A/L146A/P218T were mutants that had a large relative value for the current for irradiation with light at 600 nm. These relative values for them were at least 0.3 in all instances, and were at least 0.6-times the relative value for irradiation with light at 440 nm. L146A/P218T had two λmax_act's, which were 510 nm/560 nm, and the 440 nm relative value was obtained for the shorter wavelength side peak and the 600 nm relative value was obtained for the longer wavelength side.

As shown in FIG. 4, Y117A, Y117F, Y117N, T147C/G151A, and T147C/G151A/Y217F were also mutants that had a large relative value for the current for irradiation with light at 440 nm. For Y117A, Y117F, and T147C/G151A, this was at least 6-times, at least 6-times, and at least 18-times larger, respectively, than the relative value for irradiation with light at 600 nm. In addition, it was found that T147C/G151A/Y217F exhibited almost no current value at 600 nm, and due to this had a better response specificity on the shorter wavelength side than these mutants.

Based on the preceding, it was shown that mutants of GtCCR4, i.e., the first protein, can provide mutants favorable for color recognition.

Example 2

(Electrophysiological Measurement of ND7/23 Cells That Express GtCCR4, a Cation Channel rhodopsin Originating from *G. theta*)

With regard to the GtCCR4-expressing ND7/23 cells constructed in Example 1, the vector constructed in Example 1 was inserted into ND7/23 cells proceeding as in Example 1, and the cells for which GtCCR4 expression could be confirmed were subjected, at within 24 to 48 hours after transfection, to electrophysiological measurement by the whole-cell recording patch clamp method using the same conditions as in Example 1.

That is, the cells were irradiated with light and the following were each measured: the peak-form maximum current value (Ip) produced during irradiation with the light for a time of 400 ms, and the stationary current value (Is) provided by decay to a constant level during light irradiation. The value provided by dividing Is by Ip was termed as the channel opening ratio. The measurement principle is given in A to C of FIG. 5, and the measurement results are given in D and E of FIG. 5.

Figure 5:
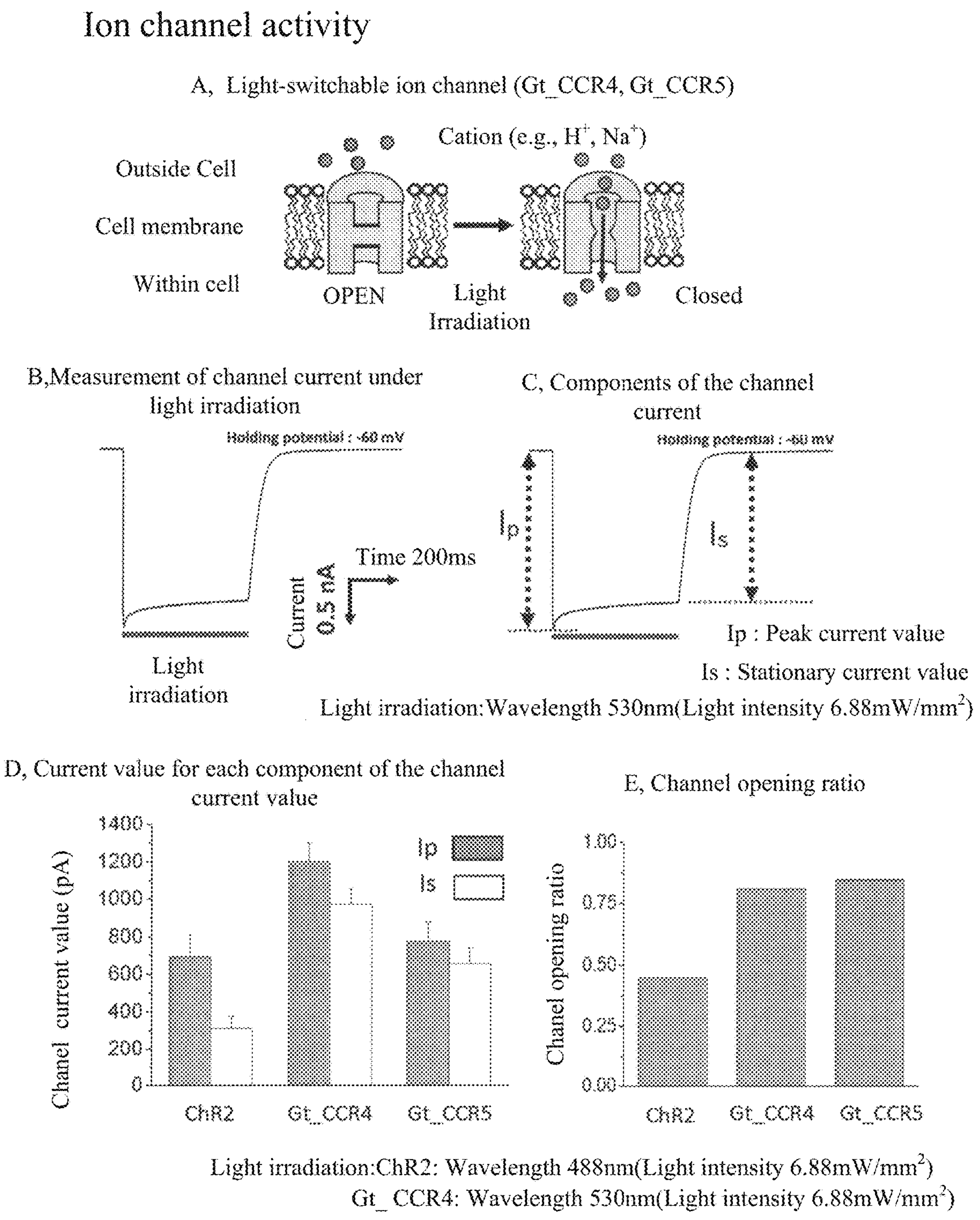
FIG. 5 provides (A) a schematic illustration of a light-gated (light-switchable) ion channel, (B) a diagram that illustrates measurement of the channel current due to irradiation with light, (C) a diagram showing the components of the channel current, and (D) a diagram giving the channel current and (E) a diagram giving the channel opening ratio tested in ND7/23 cells that express, respectively, ChR2, and GtCCR4.

As shown in D and E of FIG. 5. GtCCR4 produced a large channel current. In addition, GtCCR4 exhibited high channel opening ratios (0.81 and 0.85). Each of these characteristics is considered to contribute to a restoration of vision by targeting into ganglion cells with photosensitivity. The channel current values provided by Chlamydomonas-derived ChR2 in ND7/23 cells prepared using the same procedure was about half that of GtCCR4, and the channel opening ratio was 0.45.

Based on the preceding, GtCCR4 was found to be more favorable in terms of ion channel activity and/or channel opening ratio than those of ChR2.

Example 3

(Construction of Vectors Containing DNA Encoding GtCCR4 Mutants, Transfection of ND7/23, and Electrophysiological Measurements of Transfected Cells (1))

Single mutants provided with different single mutations were designed based on the amino acid sequence for GtCCR4 (SEQ ID NO: 1). The base sequences encoding these were established using the previously indicated codon usage, and production was carried out using the QuickChange procedure (QuikChange Site-Directed Mutagenesis Kit, Agilent Technologies, Inc.). The substitution mutations in the single mutants are given in FIG. 6.

The DNA fragments were prepared as in Example 1, the pEGFP vectors were produced by an In-Fusion reaction as in Example 1, and ND7/23 cells were transfected proceeding as in Example 2 to acquire transfected cells that expressed each single mutant. Electrophysiological measurements were performed on these transfected cells also proceeding as in Example 1. As a control, the same measurements were performed on cells transfected with Chlamydomonas-derived ChR2 and on cells transfected with wild-type GtCCR4. The results are shown in FIG. 6.

Figure 6:
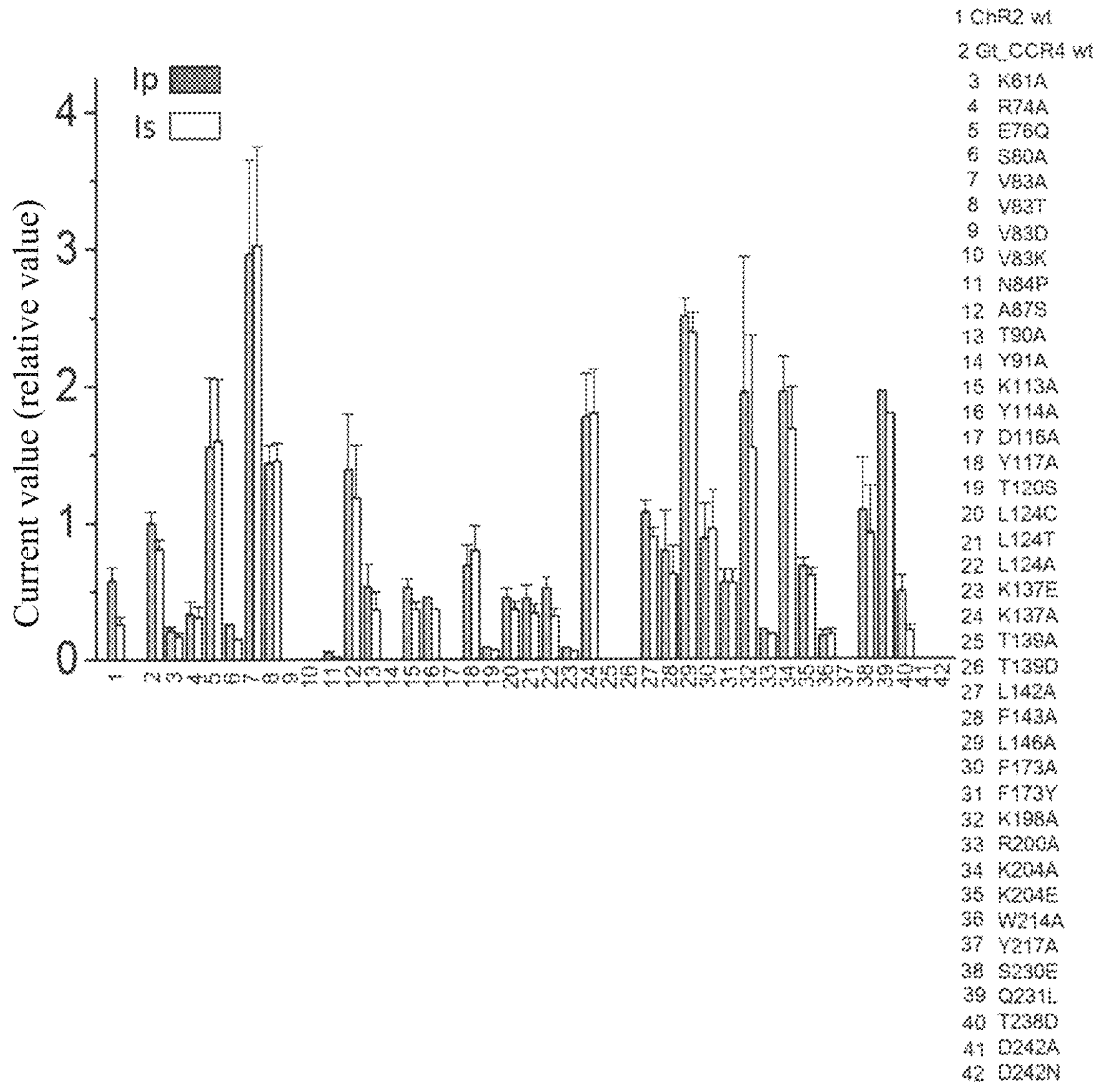
FIG. 6 is a diagram that exhibits the measurement of the channel current in ND7/23 cells that express a single mutant of GtCCR4.

As shown in FIG. 6, a number of mutants gave better results for the ion channel current value than that of the wild type. For example, E76Q, V83A, V83T, A87S, K137A, L146A, K198A, K204A, S230E, and Q231L gave a higher Ip and Is. Among these, E76Q, V83A, V83T, K137A, L146A, K198A, K204A, and Q231L exhibited a better channel activity than the wild type. E76Q, V83A, V83T, K137A, and L146A also had a channel opening ratio of approximately 1.

Based on these results, the indicated mutation positions were all shown to be mutation positions useful for controlling the channel activity in GtCCR4. These mutation positions and amino acid substitution residues were shown to be favorable amino acid substitution mutations in terms of the channel activity and/or the channel opening ratio.

Even for those mutations that exhibited the same channel activity as the wild-type GtCCR4, these still exhibited a sufficiently higher channel activity and/or channel opening ratio than those of Chlamydomonas-derived ChR2 and were considered to be useful mutation positions and substitution residues.

Example 4

(Construction of Vectors Containing DNA Encoding GtCCR4 Mutants. Transfection of ND7/23, and Electrophysiological Measurements on Transformed Cells (2))

Figure 7:
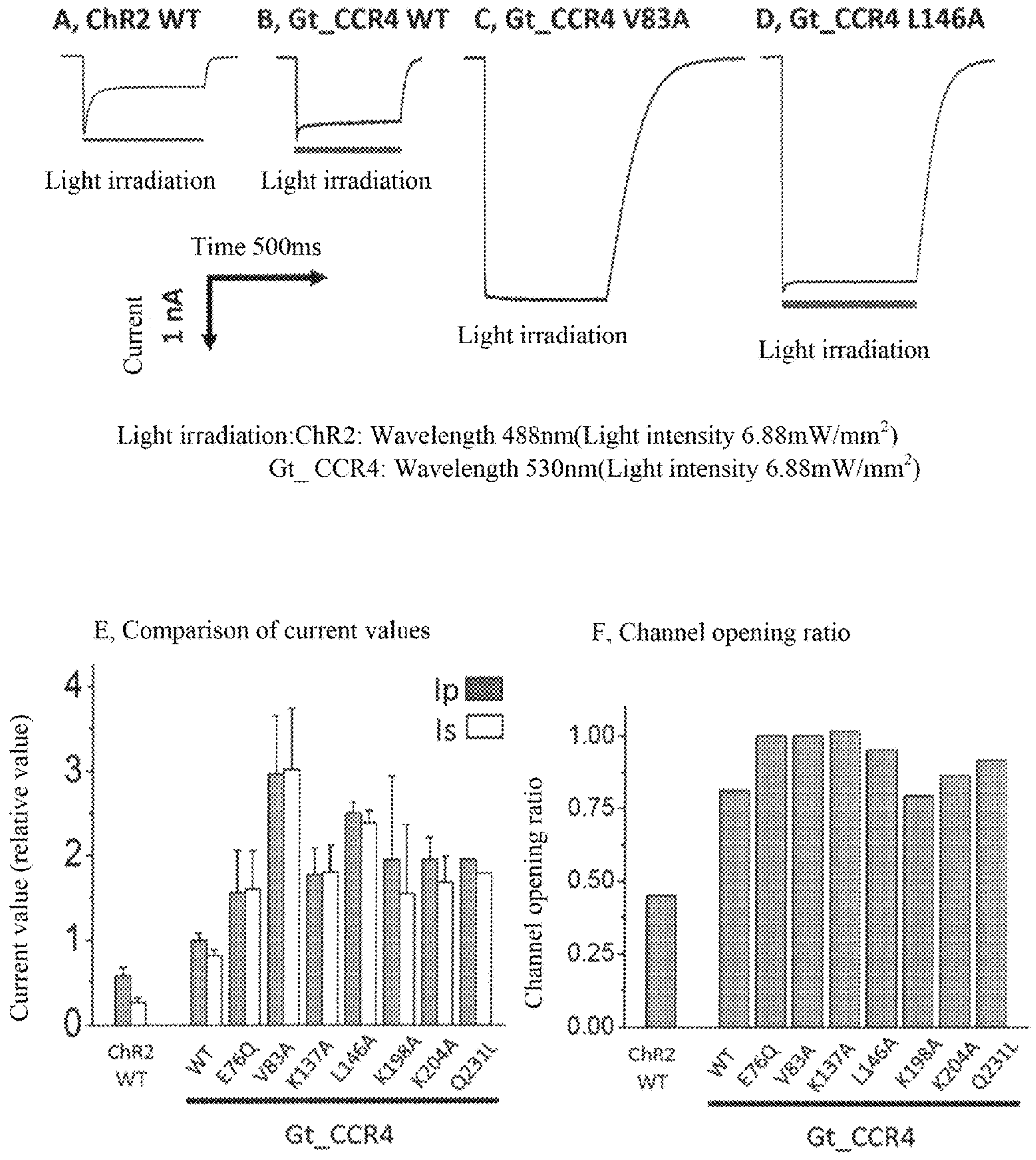
FIG. 7 provides (A) a diagram that exhibits measurement result of the channel activity in ND7/23 cells that express wild-type ChR2; (B) a diagram that gives the measurement result of the channel activity in ND7/23 cells that express wild-type GtCCR4; (C) a diagram that gives the measurement result of the channel activity in ND7/23 cells that express a GtCCR4 hearing a single mutation of V83A: (D) a diagram that gives the measurement of the channel activity in ND7/23 cells that express a GtCCR4 hearing a single mutation of L146A; and (E, F) diagrams that give the measurement results of the channel activity in ND7/23 cells that express ChR2, the wild type of GtCCR4, and GtCCR4 hearing single mutations, that provides an improvement in the relative activity.

Electrophysiological measurements were performed on each of the transfected cell populations, prepared in Example 3, that expressed a single mutant having a single amino acid substitution, i.e., E76Q, V83A, K137A, L146A, K198A, K204A, and Q231L. The electrophysiological measurements were similarly performed for Chlamydomonas-derived ChR2, wild-type GtCCR4, and the V83A mutant-transformed cells prepared in Example 3. The conditions for light exposure were as indicated in FIG. 7. The results are given in FIG. 7.

The results for Chlamydomonas-derived ChR2, wild-type GtCCR4, the V83A mutant, and the L146A mutant are given as examples in A to D of FIG. 7, and the results for each of the mutants are given in E and F of FIG. 3. As shown in A to F of FIG. 7, relative to ChR2 and wild-type GtCCR4, the various mutants not only had higher channel current values, but also had larger channel opening ratios, indicating that an inhibition of channel deactivation could be realized. An inhibition of deactivation is thought to be favorable for improving photosensitivity since the overall amount of channel current that flows is then increased.

Based on the preceding, these mutants were all considered to be highly useful mutants, and these mutation positions and substitution residues were expected to contribute to gain the channel activity and channel opening ratio.

Example 5

(Construction of Vectors Containing DNA Encoding Double Mutants in GtCCR4, Transfection of ND7/23, and Electrophysiological Measurements on Transformed Cells)

Vectors were constructed based on Examples 1 and 2 for certain combinations of the single mutations validated in Example 3 and Example 4, and electrophysiological measurements were performed as in Example 2. At the same time, the electrophysiological measurements were also performed on cells transformed by Chlamydomonas-derived ChR2 and cells transformed by wild-type GtCCR4. The results are given in FIG. 8.

Figure 8:
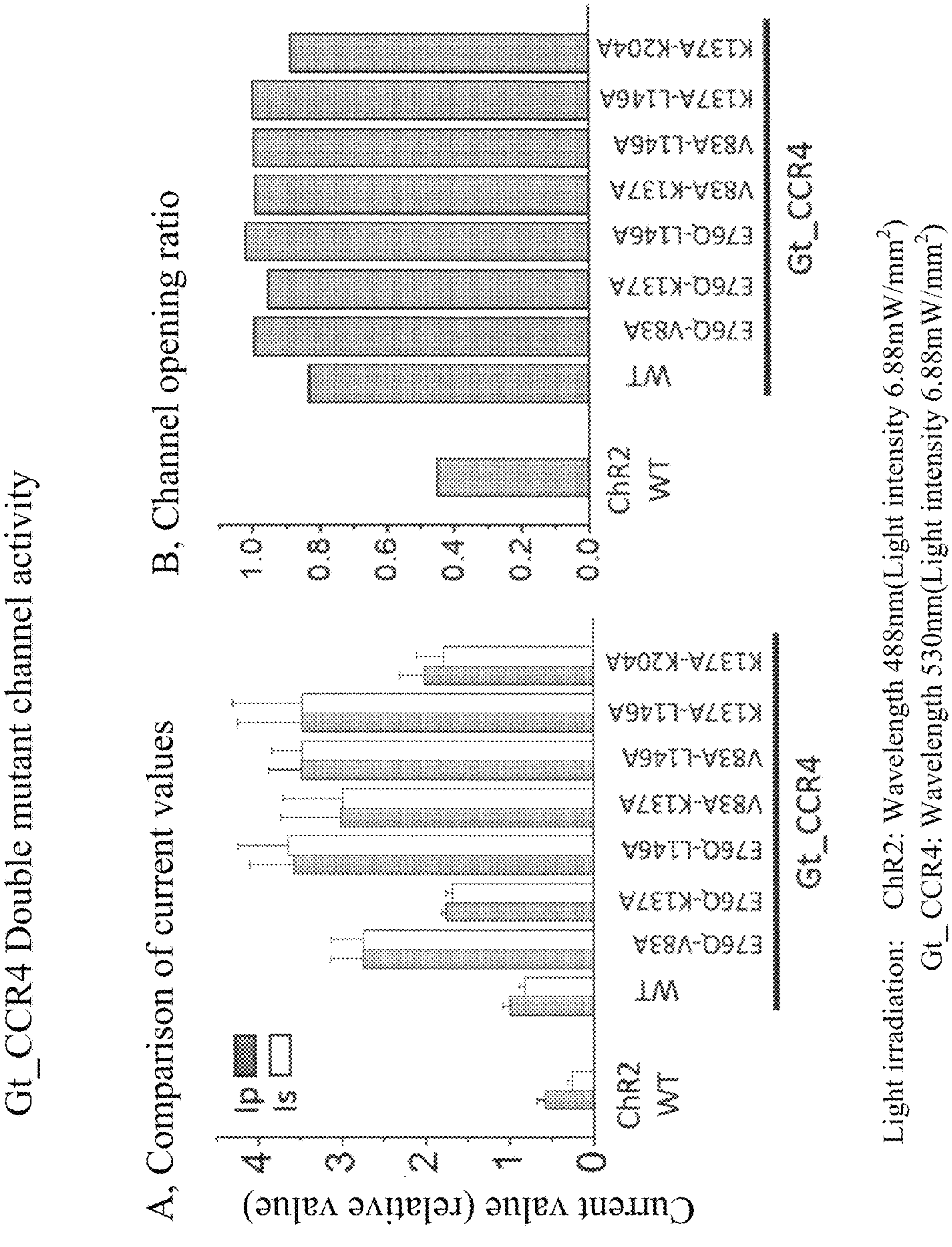
FIG. 8 is a diagram that shows the channel current (A) and the channel opening ratio (B) of ND7/23 cells that express a double mutant having two mutations in GtCCR4.

As shown in A of FIG. 8, the double mutants exhibited channel activity that was approximately 2- to 4-times higher than that of wild-type GtCCR4. As shown in B or FIG. 8, their channel opening ratios also exceeded compared to that of wild-type GtCCR4 and reached 0.9 to 1.0. Based on the preceding, it was demonstrated that, in addition to these single mutations being useful individual mutation positions and substitution residues, the double mutants were also useful mutation positions and substitution residues. Accordingly, the mutation positions and substitution residues that were excellent as single mutations were shown to also be useful in the form of double mutants.

Example 6

(Construction of Vectors Containing DNA Encoding GtCCR4 Mutants, Transfection of ND7/23, and Electrophysiological Measurements of Transformed Cells (3))

Single mutants provided with different single mutations were designed in accordance with Example 3 and based on the amino acid sequence for GtCCR4 (SEQ ID NO: 1). The base sequences encoding these were established using the previously indicated codon usage, and DNA fragments were produced using the QuickChange procedure. Then, in accordance with Example 2, pEGFP vectors were constructed using the In-Fusion reaction; ND7/23 cells were transfected to acquire transformed cells that expressed each particular single mutant; and electrophysiological measurements were carried out on these transfected cells. As a control, measurements were also similarly performed on cells transformed with the wild-type GtCCR4. The substitution mutations in the single mutants and the results of the electrophysiological measurements are given in FIG. 9.

Figure 9:
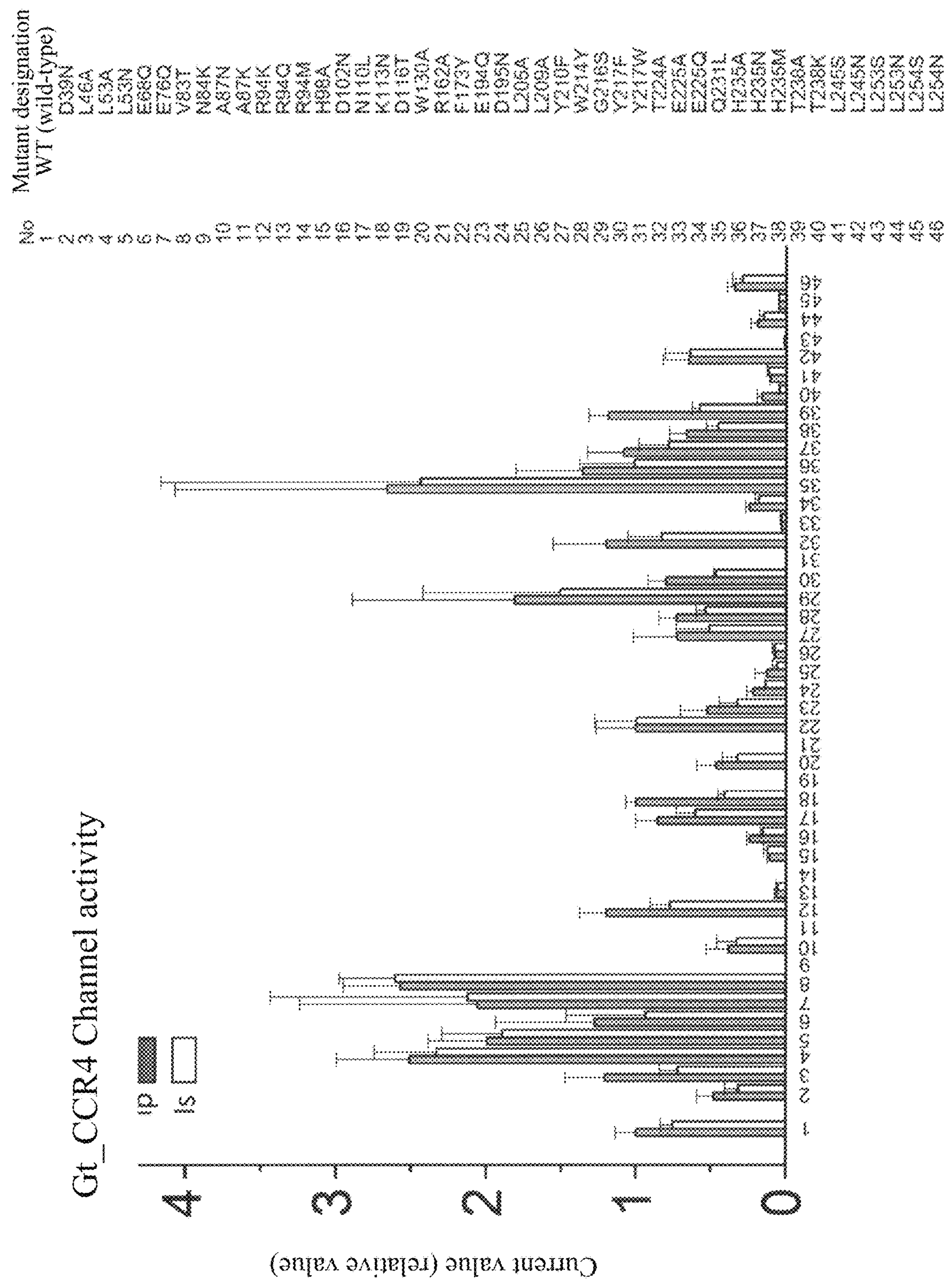
FIG. 9 is a diagram that shows the measurement results of the channel current in ND7/23 cells that express GtCCR4s bearing various single mutations.

As shown in FIG. 9, a number of the mutants exhibited results for the channel current value that were superior to those for the wild type. For example, L53A. L53N. E76Q, V83T. G216S, and Q231L gave higher Ip and Is values. These mutants also all gave a better channel opening ratio (Is/Ip). In particular, L53A, L53N, E76Q, V83T, and Q231L also had channel opening ratios of approximately 1. Viewed from the standpoint of activity. L53A, V83T, and Q231L were excellent.

In addition, the activities of L46A, E68Q, R94K, F173Y, T224A, H235A, and H235N were about equal to that of the wild type, but were considered to have achieved channel activity and/or channel opening ratio that was sufficiently higher than that of Chlamydomonas-derived ChR2, and due to this were regarded as useful mutation positions and substitution residues.

Based on the preceding, the mutation positions indicated above were all shown to be mutation positions useful for controlling the channel activity of GtCCR4. The mutation positions and amino acid substitution residues indicated above were shown to be amino acid substitution mutations favorable in terms of the channel activity and/or channel opening ratio.

Example 7

(Nerve Cell Photostimulation Experiments)

In this example, light at a wavelength that induces a response was irradiated, at different light intensities, onto rat cerebral epithelial primary cultured cells expressing a photosensitive protein in the cell membrane. The cell membrane potential was measured and the dependence of the photostimulation on the light intensity was evaluated.

Here, photostimulation refers to activation (firing, excitation) due to exposure of the nerve cells to light. In this example, an experiment was performed using the electrophysiological procedure described below as the method for evaluating photostimulation. Thus, rat cerebral epithelial cells were isolated and cultured on a dish. This is referred to as primary cultured cells. After the expression in these primary cultured cells of GtCCR4(WT) or ChR2(WT) in accordance with Examples 1 and 2, etc., exposure to light at different intensities and at the maximum absorption wavelength of 530 nm and 488 nm, respectively, was carried out for a prescribed period of time. During this, excitation (depolarization) and hyperpolarization (inhibition) were measured on single nerve cells using the current-clamped whole-cell recording patch clamp method and the time course of the cell membrane potential was measured.

Specifically, DNA encoding the particular amino acid sequence for GtCCR4 or ChR2 was synthesized (using a mammalian codon usage); a plasmid for transfection was created by the incorporation in a CAMK2 promoter-bearing vector plasmid for nerve cells, in such a manner that eYFP was tagged at the C-terminal of the particular protein: and this plasmid was transfected by transfection, using the calcium phosphate method, into the rat cerebral epithelial primary cultured cells. The expression of the particular protein in the cell membrane of the recipient cells could be confirmed by eYFP fluorescence.

Using the cells in which, proceeding in this manner, the particular protein was transiently expressed in the membrane of the primary cultured cells, the electrophysiological measurement, e.g., by the whole-cell recording patch clamp method, was performed within 16 days after transfection, in a state in which the particular protein was stably expressed.

The following conditions were adopted for the measurement conditions in the current-clamped whole-cell recording patch clamp method.

TABLE 9

| | |
|---|---|
| (1) head stage-equipped current amplifier | IPA patch clamp amp (Sutter Instrument) |
| (2) software | control software: Igor 8.0; analytic software: Igor 8.0 |
| (3) microscope | IX-73 or IX-70 (Olympus) |
| (4) glass pipette | Produced by processing a glass capillary tube using a Micropipetter Puller P-97 (Sutter Instrument) and carrying out fire polishing using an MF-830 (Narishige). Pipette resistance: 5 to 10 MΩ |
| (5) micromanipulator | NMN-21 manipulator (Narishige) |
| (6) extracellular solution | 138 mM NaCl, 3 mM KCl, 10 mM HEPES, 4 mM NaOH, 2 mM $CaCl_2$, 1 mM $MgCl_2$, 11 mM glucose, 20 mM 6,7-dinitroquinoxaline-2,3-dione (DNQX), 25 mM D-(−)-2-amino-5-phosphonovaleric acid (D-AP5), and 100 mM picrotoxin, pH 7.4 |
| (7) intracellular solution | 125 mM K-gluconate, 10 mM NaCl, 0.2 mM EGTA, 10 mM HEPES, 1 mM $MgCl_2$, 3 mM MgATP, 0.3 mM $Na_2GTP$, 10 mM $Na_2$-phosphocreatine, 0.1 mM Leupeptin, pH 7.4 |
| (8) current recording conditions | irradiated light: 530 nm (GtCCR4) and 488 nm (ChR2), light intensity: 6.9 $mW/mm^2$, irradiation time: 100 ms to 600 ms, recording time: 300 ms to 1000 ms, room temperature |

The measurement procedure was as follows. The solution in the prepared cell plate was replaced with the extracellular solution according to (6) above. The cells were then observed under a microscope, and cells that strongly emitted eYFP fluorescence were selected. The inner channel of the glass pipette, which was produced according to (4) above, was filled with the intracellular solution according to (7) above and was connected to the head stage attached to the current amplifier according to (1). By manipulating the position of the glass pipette with the micromanipulator described in (5) above, the tip of the glass pipette was moved to about 2-3 microns above the cell. The glass pipette was gradually lowered by operation of the micromanipulator and was moved to a position where the cell and the tip of the pipette were in contact. The pressure within the glass pipette was then reduced to bring the cell membrane into complete close contact with the pipette tip. The pipette resistance at this time, which had been 5 to 10 MΩ, rises to about 1 GM. A whole cell mode that enabled whole cell recording was provided by reducing the pressure in pipette.

After the state described above had been achieved, the cell membrane potential was measured using the current-clamped patch clamp method. When the nerve cell was in the resting state, the membrane potential exhibited a value of −70 to −80 mV; however, when the light was illuminated on a cell that expressed the protein having photoresponse activity, the cell underwent depolarization and because of this the membrane potential rose to −20 to −40 mV and a spike-form nerve activation (excitation, firing) was then observed. A photostimulation by these proteins was confirmed by measuring the degree of depolarization during measurement under these conditions, i.e., by measuring the frequency of spike-form nerve firing. The results are given in FIG. 10.

Figure 10:
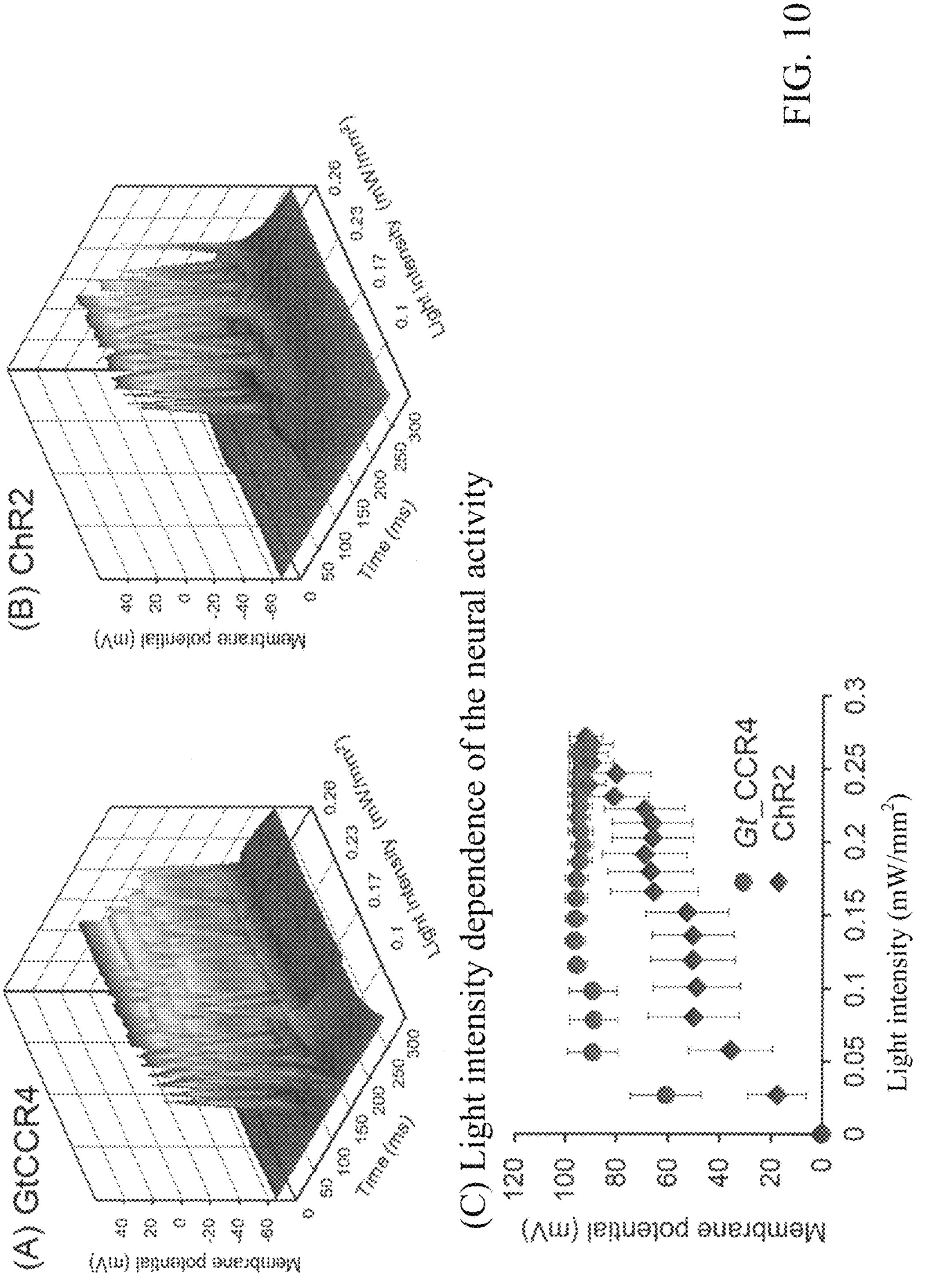
FIG. 10 is a diagram that shows experimental results of the photostimulation of the neural activity in primary cultured rat cerebral epithelial cells that express GtCCR4 (A) and ChR2 (B), and (C) comparative results for the dependence on the light intensity.

As indicated in (A) to (C) in FIG. 10, it was demonstrated that activation occurred with GtCCR4 at a lower light intensity than for ChR2. When the EC50 was compared, the difference was at least 7-fold with 0.02 $mW/mm^2$ for GtCCR4 and 0.15 $mW/mm^2$ for ChR2. This means that GtCCR4 has a light sensitivity at least 7-fold higher than that of ChR2. Based on the preceding, it was thus demonstrated that a GtCCR4 mutant for which activity at least equal to that of the wild-type GtCCR4 has been confirmed, has the same light intensity dependence as the wild-type GtCCR4, i.e., even at low light intensities, a photostimulation capability exists for cells that satisfactorily express such a protein in the membrane.

This Description encompasses the following disclosures.

(1) A protein having a channel activity and comprising an amino acid residue different from the amino acid residue present in a first amino acid sequence represented by SEQ ID NO: 1, at a position or positions corresponding to one or two or more selections from the group consisting of the following positions in the first amino acid sequence: positions 53, 83, 87, 117, 120, 124, 137, 139, 142, 143, 146, 150, 169, 173, 177, 198, 204, 216, 217, 218, 231, 238, 245, and 247.

(2) The protein according to (1), wherein said position or positions is or are one or two or more selections from the group consisting of positions 87, 117, 120, 124, 139, 142, 143, 146, 150, 169, 173, 177, 217, 218, 238, 245, and 247.

(3) The protein according to (1), wherein said position or positions is or are one or two or more selections from the group consisting of positions 53, 83, 137, 146, 169, 177, 217, 218, and 247.

(4) The protein according to (3), wherein said position or positions is or are one or two or more selections from the group consisting of positions 169, 177, 217, 218, and 247.

(5) The protein according to (4), having a maximum activity wavelength of less than 520 nm.

(6) The protein according to (3), wherein said position or positions is or are one or two or more selections from the group consisting of positions 53, 83, 137, 146, and 218.

(7) The protein according to (6), having a maximum activity wavelength of at least 530 nm.

(8) The protein according to (1), wherein said position or positions is or are one or two or more selections from the group consisting of positions 137, 146, 150, 177, 198, 238, 245, and 247.

(9) The protein according to (8), having a maximum activity wavelength of greater than or equal to 520 nm and less than 530 nm.

(10) The protein according to (1) or (2), wherein said position or positions is or are one or two or more selections from the group consisting of positions 150, 169, 177, 218, and 247.

(11) The protein according to (1), wherein said position or positions is or are one or two or more selections from the group consisting of positions 87, 117, 120, 124, 139, 142, 143, 173, 204, 216, and 231.

(12) The protein according to any of (1) to (11), further comprising a deletion, substitution, or insertion of one or several amino acid residues.

(13) The protein according to any of (1) to (12), wherein the protein comprises an amino acid substitution according to any of the following modes, at a position corresponding to a position as follows in the first amino acid sequence.

TABLE 10

| position in first amino acid sequence | amino acid substitution mode | | | |
|---|---|---|---|---|
| 53 | L53N | | | |
| 83 | V83A | | | |
| 137 | K137A | | | |
| 146 | L146A | | | |
| 150 | C150A | | | |
| 169 | G169S | | | |
| 177 | W177Y | | | |
| 198 | K198A | | | |
| 217 | Y217F | Y217N | | |
| 218 | P218A | P218S | P218G | P218T |
| 238 | T238V | | | |
| 245 | A245M | | | |
| 247 | S247A | S247M | | |
| 146/150 | L146A/C150A | | | |
| 146/169 | L146A/G169S | | | |
| 146/177 | L146A/W177Y | | | |
| 146/217 | L146A/Y217F | | | |
| 147/218 | L146A/P218A | L146A/P218T | L146A/P218S | L146A/P218G |
| 146/238 | L146A/T238V | | | |
| 83/146/218 | V83A/L146A/P218A | | | |

(14) The protein according to any of (1) to (12), wherein the protein comprises an amino acid substitution according to any of the following modes, at a position corresponding to a position as follows in the first amino acid sequence.

TABLE 11

| position in first amino acid sequence | amino acid substitution mode | | | |
|---|---|---|---|---|
| 53 | L53A | | | |
| 83 | V83T | | | |
| 87 | A87S | | | |
| 117 | Y117A | Y117D | Y117F | Y117N |
| 124 | L124Q | L124C | L124T | L124A |
| 142 | L142A | | | |
| 204 | K204A | | | |
| 216 | G216S | | | |
| 231 | Q231L | | | |
| 137/204 | K137A/K204A | | | |
| 146/218 | L146A/P218C | L146A/P218H | L146A/P218N | L146A/P218V |

(15) The protein according to any of (1) to (14), for which a first ratio, this being a value corresponding to a channel activity at 440 nm relative to the value corresponding to the channel activity at the wavelength (λmax) at which the protein exhibits its maximum channel activity, is greater than or equal to 0.4.

(16) The protein according to any of (1) to (15), for which a second ratio, this being a value corresponding to a channel activity at 600 nm relative to the value corresponding to the channel activity at the wavelength (λmax) at which the protein exhibits its maximum channel activity, is greater than or equal to 0.4.

(17) The protein according to any of (1) to (16), wherein the amino acid sequence of the protein has 90% or more identity with the first amino acid sequence.

(18) A method of use to improve or recover a photosensitivity for color recognition of a retina, using a protein according to any of (1) to (17) or a polynucleotide that encodes said protein.

(19) A drug composition for the treatment or prevention of a visual impairment, comprising a protein according to any of (1) to (17) or a polynucleotide that encodes said protein.

(20) The drug composition according to (19), wherein the visual impairment is selected from the group consisting of retinitis pigmentosa, age-related macular degeneration, retinal detachment, diabetic retinopathy, and color vision abnormalities.

(21) A method for screening mutant proteins, comprising a step of evaluating a relationship between the wavelength of irradiated light and a channel activity for a test protein that is provided with an amino acid residue different from that in the first amino acid sequence represented by SEQ ID NO: 1, at one or two more positions in the first amino acid sequence.

Sequence Listing Free Text

SEQ ID NOS: 3 to 6: primer

Sequence Listing

The invention claimed is:

1. A protein comprising an amino acid sequence having at least 98% identity to SEQ ID NO. 1, wherein the amino acid sequence comprises one or more amino acid substitutions selected from (i) Y117F; (ii) L146A and Y217F; and (iii) T147C, G151A, and Y217F, at the position or positions corresponding to the one or more positions in the amino acid sequence represented by SEQ ID NO: 1, and wherein the protein has a channel activity and wherein the λmax wavelength of the protein is shorter than the λmax wavelength of the protein consisting of the amino acid sequence of SEQ ID NO: 1.

2. The protein according to claim 1, wherein the amino acid sequence comprises the amino acid substitution Y117F.

3. The protein according to claim 1, wherein the amino acid sequence comprises acid substitutions selected from (ii) L146A and Y217F; and (iii) T147C, G151A, and Y217F.

4. The protein according to claim 1, wherein the amino acid sequence of the protein has 99% or more identity with SEQ ID NO: 1.

5. A method of improving a photosensitivity for color recognition of a retina, comprising providing a protein according to claim 1, a polynucleotide that encodes the protein, or a vector comprising the polynucleotide to retinal cells of a patient in need thereof.

6. A method of treating visual impairment, comprising providing a protein according to claim 1, a polynucleotide that encodes the protein, or a vector comprising the polynucleotide to retinal cells of a patient of visual impairment.

7. The method according to claim 6, wherein the visual impairment is selected from the group consisting of retinitis pigmentosa, age-related macular degeneration, diabetic retinopathy, retinal detachment, and color vision abnormalities.

* * * * *